US005849533A

United States Patent [19]
Berman et al.

[11] Patent Number: 5,849,533
[45] Date of Patent: Dec. 15, 1998

[54] METHOD FOR MAKING UNCLIPPED HIV ENVELOPE PROTEIN

[75] Inventors: Phillip W. Berman, Portola Valley; Brian M. Fendly, Half Moon Bay; Timothy J. Gregory, Hillsborough; Elorian M. Wurm, Foster City, all of Calif.

[73] Assignee: Genetech, Inc., S. San Francisco, Calif.

[21] Appl. No.: 802,361

[22] Filed: Feb. 19, 1997

Related U.S. Application Data

[60] Continuation of Ser. No. 226,162, Apr. 11, 1994, Pat. No. 5,674,984, which is a division of Ser. No. 101,669, Aug. 2, 1993, abandoned, which is a continuation of Ser. No. 834,735, Feb. 13, 1992, abandoned, which is a division of Ser. No. 504,785, Apr. 3, 1990, abandoned.

[51] Int. Cl.$^6$ .............................. C12P 21/00; C12P 21/02
[52] U.S. Cl. ................. 435/69.3; 424/188.1; 424/208.1; 435/172.3; 530/412; 530/413
[58] Field of Search .............................. 424/148.1, 160.1, 424/188.1, 208.1; 435/69.3, 172.3, 325, 352, 358, 362, 320.1; 530/412, 413

[56] References Cited

U.S. PATENT DOCUMENTS

| 4,725,669 | 2/1988 | Essex ....................................... 530/322 |
| 5,166,050 | 11/1992 | Shriver et al. .............................. 435/5 |

FOREIGN PATENT DOCUMENTS

| 187041 | 7/1986 | European Pat. Off. . |
| 335635 | 4/1989 | European Pat. Off. . |
| 339504 | 11/1989 | European Pat. Off. . |
| WO 89/12095 | 12/1989 | WIPO . |
| WO 90/02196 | 3/1990 | WIPO . |
| WO 91/13906 | 9/1991 | WIPO . |
| WO 93/20104 | 10/1993 | WIPO . |

OTHER PUBLICATIONS

Allan, et al., "Major glycoprotein antigens that induce antibodies in AIDS patients are encoded by HTLV–III" *Science* 228(4703):1091–1094 (May 1985).
Anderson et al., "Effect of Dose and Immunization Schedule on Immune Response of Baboons to Recombinant Glycoprotein 120 of HIV–1" *J. Infectious Diseases* 160(6):960–969 (1989).
Arthur et al., "Challenge of Chimpanzees (Pan Troglodytes) Immunized with Human Immunodeficiency Virus Envelope Glycoprotein gp120" *Journal of Virology* 63(12):5046–5053 (1989).
Barin et al., "Virus Envelope Protein of HTLV–III Represents Major Target Antigen for Antibodies in AIDS Patients" *Science* 228:1094–1096 (1985).
Barrett et al., "Large–Scale Production and Purification of a Vaccinia Recombinant–Derived HIV–1 gp160 and Analysis of Its Immunogenicity" *AIDS Research and Human Retroviruses* 5(2):159–171 (1989).

Berman et al., "Expression and Immunogenicity of the Extracellular Domain of the Human Immunodeficiency Virus Type 1 Envelope Glycoprotein, gp160" *Journal of Virology* 63(8):3489–3498 (1989).
Berman et al., "Human Immunodeficiency Virus Type 1 Challenge of Chimpanzees Immunized with Recombinant Envelope Glycoprotein gp120" *Proc. Natl. Acad. Sci. USA* 85(14):5200–5204 (Jul. 1988).
Berman et al., "Protection from Genital Herpes Simplex Virus Type 2 Infection by Vaccination with Cloned Type 1 Glycoprotein D" *Science* 227(4693):1490–1492 (Mar. 22, 1985).
Berman et al., "Protection of Chimpanzees from Infection by HIV–1 after Vaccination with Recombinant Glycoprotein gp120 But not gp160" *Nature* 345(6276):622–625 (Jun. 14, 1990).
Celltech, "CHO cell rgp120" *Certificate of Analysis* pp. 1–2 (Jan. 1990).
Chakrabarti et al., "Expression of the HTLV–III Envelope Gene by a Recombinant Vaccinia Virus" *Nature* 320:535–540 (1986).
Clements et al., "The V3 Loops of the HIV–1 and HIV–2 Surface Glycoproteins Contain Proteolytic Cleavage Sites: A Possible Function in Viral Fusion" *AIDS Research and Human Retroviruses* 7:3–16 (1991).
Desrosiers et al., "Vaccine Protection Against Simian Immunodeficiency Virus Infection" *Proc. Natl. Acad. Sci. USA* 86:6353–6357 (Aug. 1989).
Fahey et al., "Status of Immune–based Therapies in HIV Infection and AIDS" *Clin. Exp. Immunology* 88:1–5 (1992).
Fauci et al., "Development and Evaluation of a Vaccine for Human Immunodeficiency Virus (HIV) Infection" *Annals of Internal Medicine* 110(5):373–385 (Mar. 1989).
Homsy et al., "The Fc and Not CD4 Receptor Mediates Antibody Enhancement of HIV Infection in Human Cells" *Science* 244:1357–1359 (Jun. 1989).
Hu et al., "Effect of Immunization with a Vaccinia–HIV env Recombinant on HIV Infection of Chimpanzees" *Nature* 328(6132):721–723 (Aug. 1987).
Hu et al., "Expression of AIDS Virus Envelope Gene in Recombinant Vaccinia Viruses" *Nature* 320:537–540 (1986).
Javaherian et al., "Principal Neutralizing Domain of the Human Immunodeficiency Virus Type 1 Envelope Protein" *Proc. Natl. Acad. Sci. USA* 86(17):6768–6772 (Sep. 1989).
Kitchen et al., "Aetiology of AIDS—antibodies to human T–cell leukaemia virus (type III) in haemophiliacs" *Nature* 312:367–369 (1984).

(List continued on next page.)

*Primary Examiner*—Robert D. Budens
*Attorney, Agent, or Firm*—Timothy E. Torchia, Ph.D.

[57] ABSTRACT

Methods for making unclipped HIV env proteins are provided. According to the methods, a genetically engineered cell line comprising an nucleic acid sequence encoding an HIV env protein is cultured to produce unclipped HIV env protein, which is recovered from the cell culture.

2 Claims, 10 Drawing Sheets

OTHER PUBLICATIONS

Krust et al., "Characterization of a monoclonal antibody specific for the HIV–1 precursor glycoprotein" *AIDS* 2:17–24 (1988).

Lasky, "Current Status of the Development of an AIDS Vaccine" *Critical Reviews in Immunology* 9(3):153–172 (1989).

Lasky et al., "Delineation of a Region of the Human Immunodeficiency Virus Type 1 gp120 Glycoprotein Critical for Interaction With the CD4 Receptor" *Cell* 50(6):975–985 (Sep. 11, 1987).

Lasky et al., "Neutralization of the AIDS Retrovirus by Antibodies to a Recombinant Envelope Glycoprotein" *Science* 233:209–212 (1986).

Letvin et al., "AIDS–like Disease in Macaque Monkeys Induced by Simian Immunodeficiency Virus: A Vaccine Trial" *Vaccines* 87:209–213 (1987).

Looney et al., "Type–restricted Neutralization of Molelcular Clones of Human Immunodeficiency Virus" *Science* 241(4863):357–359 (Jul. 15, 1988).

Matsushita et al., "Characterization of a Human Immunodeficiency Virus Neutralizing Monoclonal Antibody and Mapping of the Neutralizing Epitope" *Journal of Virology* 62(6):2107–2114 (Jun. 1988).

Modrow et al., "Computer–assisted Analysis of Envelope Protein Sequnces of Seven Human Immunodeficiency Virus Isolates: Prediction of Antigenic Epitopes in Conserved and Variable Regions" *Journal of Virology* 61(2):570–578 (1987).

Murphey–Corb et al., "A Formalin–Inactivated Whole SIV Vaccine Confers Protection in Macaques" *Science* 246:1293–1297 (Dec. 1989).

Newmark, P., "Receding Hopes of AIDS Vaccines" *Nature* 333:699 (Jun. 23, 1988).

Palker et al., "Type–specific Neutralization of the Human Immunodeficiency Virus with Antibodies to env–encoded Synthetic Peptides" *Proc. Natl. Acad. Sci. USA* 83:1932–1936 (Mar. 1988).

Prince et al., "Failure of a Human Immunodeficiency Virus (HIV) Immune Globulin to Protect Chimpanzees Against Experimental Challenge with HIV" *Proc. Natl. Acad. Sci. USA* 85(18):6944–6948 (1988).

Robey et al., "Prospect for prevention of human immunodeficiency virus infection: Purified 120–kDa envelope glycoprotein induces neutralizing antibody" *Proc. Natl. Acad. Sci.* 83:7023–7027 (1986).

Robey, W.G. et al., "Characterization of envelope and core structural gene products of HTLV–III with sera from AIDS patients" *Science* 228(4699):593–595 (May 3, 1985).

Robinson et al., "Antibody–Dependent Enhancement of Human Immunodeficiency Virus Type 1 Infection" *Lancet* 1(8589):790–794 (Apr. 1988).

Robinson et al., "Human Monoclonal Antibodies to the Human Immunodeficiency Virus Type 1" *Proc. Natl. Acad. Sci. USA* 87(8):3185–3189 (Apr. 1990).

Rusche et al., "Antibodies That Inhibit Fusion of Human Immunodeficiency Virus–Infected Cells Bind a 24–amino Acid Sequence of the Viral Envelope, gp120" *Proc. Natl. Acad. Sci. USA* 85(9):3198–3202 (May 1988).

Salk et al., "Control of Influenza and Poliomyelitis with Killed Virus Vaccines" *Science* 195(4281):834–847 (Mar. 4, 1977).

Salk, J., "Prospects for the Control of AIDS by Immunizing Seropositive Individuals" *Nature* 327(6122):473–476 (Jun. 1987).

Stephens et al., "A Chink in HIV's Armour?" *Nature* (letter) 343(6255):219 (Jan. 18, 1990).

Van Eendenburg et al., "Cell–mediated Immune Proliferative Responses to HIV–1 of Chimpanzees Vaccinated with Different Vaccinia Recombinant Viruses" *AIDS Research and Human Retroviruses* 5(1):41–50 (1989).

Vandenbark et al., "Immunization with a Synthetic T–cell Receptor V–region Peptide Protects Against Experimental Autoimmune Encephalomyelitis" *Nature* 341:541–544 (Oct. 12, 1989).

Veronese et al., "Characterization of gp41 As the Transmembrane Protein Coded by the HTLV–III/LAV–Envelope Gene" *Science* 229:1402–1405 (1985).

Zagury et al., "A Group Specific Anamnestic Immune Reaction Against HIV–1 Induced by a Candidate Vaccine Against AIDS" *Nature* 332(6166):728–731 (1988).

Zagury et al., "Immunization Against AIDS in Humans" *Nature* 326(6110):249–250 (Mar. 1987).

Zarling et al., "T–cell Responses to Human AIDS Virus in Macaques Immunized with Recombinant Vaccinia Viruses" *Nature* 323(6086):344–346 (1986).

Lasky et al., *Science* 223:209–212, Jul. 11, 1986.

Stephens et al., *Nature* 343:219, Jan. 18, 1990.

```
  1  THR GLU LYS*LEU TRP VAL THR VAL TYR TYR GLY VAL PRO VAL TRP LYS GLU ALA THR THR LEU
                  •••••••
                                    **
 23  PHE CYS ALA SER ASP ALA LYS ALA TYR ASP THR GLU VAL HIS ASN VAL TRP ALA THR HIS ALA CYS
     |————T1————|
                                                   •
 45  VAL PRO THR ASP PRO ASN PRO GLN GLU VAL VAL LEU VAL ASN VAL THR GLU ASN PHE ASN MET TRP
                                      |——————————T2——————————|

67  LYS ASN ASP MET VAL GLU GLN MET HIS GLU ASP ILE ILE SER LEU TRP ASP GLN SER LEU LYS PRO
                                                  |————T3————|
                                                           •
 89  CYS VAL LYS LEU THR PRO LEU CYS VAL SER LEU LYS CYS THR ASP LEU LYS ASN ASP THR ASN THR
                     |————T4a————|         |——T5——|
                                                                •
111  ASN SER SER GLY ARG MET ILE MET GLU LYS GLY GLU ILE LYS ASN CYS SER PHE ASN ILE SER
     |——T6——|                                  |————T8————|            |——T9——|

133  THR SER ILE ARG GLY LYS VAL GLN LYS GLU TYR ALA PHE PHE TYR LYS LEU ASP ILE ILE PRO ILE
                                            |————————T10————————|
            •
155  ASP ASN ASP THR THR SER TYR THR LEU THR SER CYS ASN THR SER VAL ILE THR GLN ALA CYS PRO
                                       |————————T11————————|
```

FIG. 2A-1

```
177  LYS VAL SER PHE GLU PRO ILE HIS TYR CYS ALA PRO ALA GLY PHE ALA ILE LEU LYS CYS
                |---T12a---|                    |---T12b---|              |---T12c---|

199  ASN ASN LYS THR PHE ASN GLY THR GLY PRO CYS THR ASN VAL SER THR VAL GLN CYS THR HIS GLY
        |---T13---|                           |---T14a---|

221  ILE ARG PRO VAL VAL SER THR GLN LEU LEU LEU ASN GLY SER LEU ALA GLU GLU VAL VAL ILE
                                           |---T14b---|

243  ARG SER ALA ASN PHE THR ASP ASN ALA LYS THR ILE ILE VAL GLN LEU ASN GLN SER VAL GLU ILE
                    |---T15---|                                |---T16---|

265  ASN CYS THR ARG PRO ASN ASN ASN THR ARG LYS SER ILE ARG ILE GLN ARG GLY PRO GLY ARG ALA
            |---T17---|                   |---T18---|         |---T19---|

287  PHE VAL THR ILE GLY LYS ILE GLY ASN MET ARG GLN ALA HIS CYS ASN ILE SER ARG ALA LYS TRP
        |---T20---|             |---T21---|                 |---T22---|         |---T23---|

309  ASN ASN THR LEU LYS GLN ILE ASP SER LYS LEU ARG GLU GLN PHE GLY ASN ASN LYS THR ILE ILE
        |---T24---|             |---T25---|             |---T26---|                 |---T27---|

331  PHE LYS GLN SER SER GLY GLY ASP PRO GLU ILE VAL THR HIS SER PHE ASN CYS GLY GLY GLU PHE
```

```
353  PHE TYR CYS •ASN SER THR GLN LEU PHE •ASN SER THR TRP PHE •ASN SER THR TRP SER THR GLU GLY
                                           |————————————T28————————————|

375  SER •ASN ASN THR GLU GLY SER ASP THR ILE THR LEU PRO CYS ARG ILE LYS GLN PHE ILE ASN MET
                              |——————T29——————|              |——————————T30——————————|

397  TRP GLN GLU VAL GLY LYS ALA MET TYR ALA PRO PRO ILE SER GLY GLN ILE ARG CYS SER SER •ASN
                                                         |——————————T32——————————

419  ILE THR GLY LEU LEU THR ARG ASP GLY GLY ASN ASN ASN GLU SER GLU ILE PHE ARG PRO
     |——————T31——————|    |—————————————————————————T32—————————————————————————|

441  GLY GLY GLY ASP MET ARG ASP ASN TRP ARG SER GLU LEU TYR LYS TYR LYS VAL VAL LYS ILE GLU
     |————T33————|    |—————————————T34—————————————|    |————T35————|    |————T36————|

463  PRO LEU GLY VAL ALA PRO THR LYS ALA LYS ARG ARG VAL VAL GLN ARG GLU 479
     |————————————T37————————————|    |——————————T38——————————|
```

FIG. 2B

```
9AA   1  LYS TYR ALA LEU ALA ASP ALA SER LEU 9
                                           *

CL44  1  LYS TYR ALA LEU ALA ASP ALA SER LEU LYS MET ALA ASP PRO ASN ARG
         |————H1————|                       |————H2————|

PHE ARG GLY LYS ASP LEU PRO VAL LEU ASP GLN**27
         |——H3——|  |——H4——|   |————T2————|
```

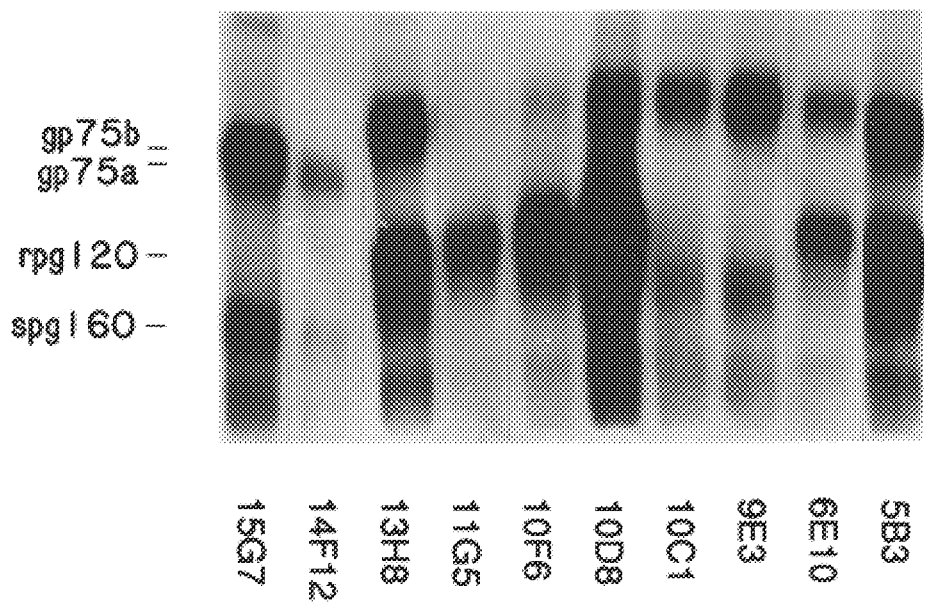

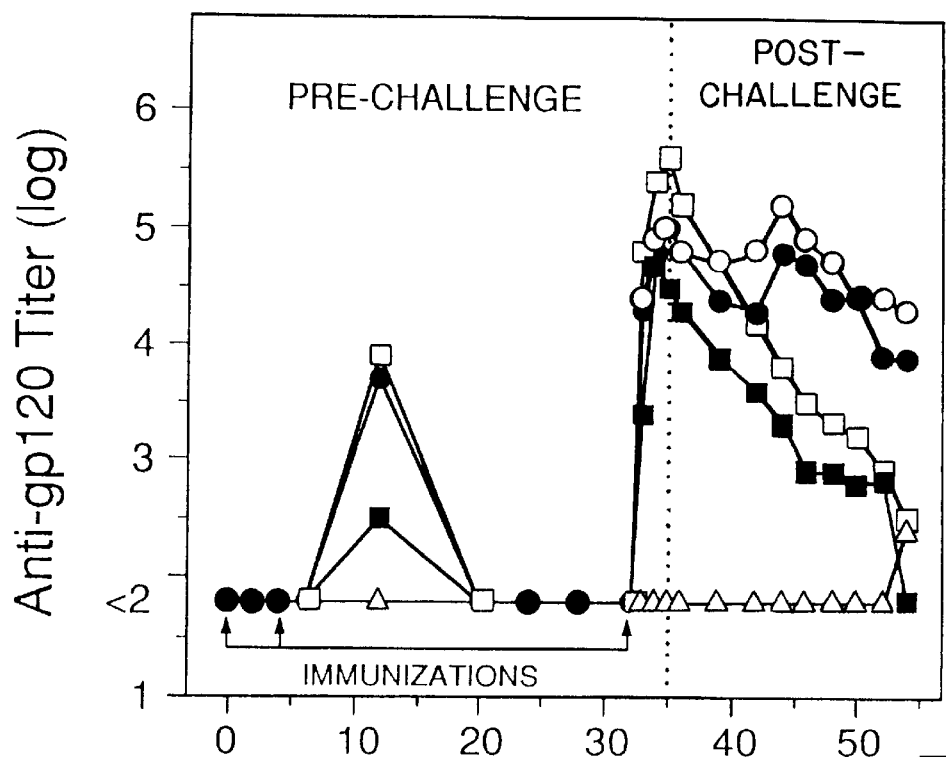
FIG. 6A
FIG. 6B
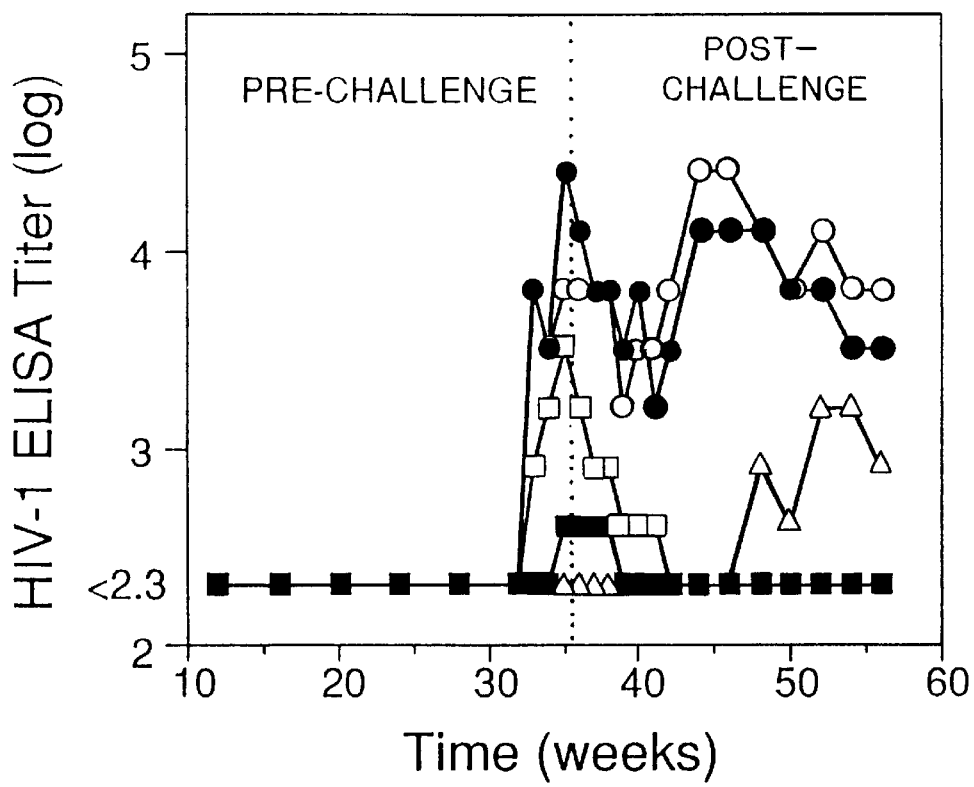

METHOD FOR MAKING UNCLIPPED HIV ENVELOPE PROTEIN

This is a continuation of application(s) Ser. No. 08/226,162 filed on Apr. 11, 1994 now U.S. Pat. No. 5,674,984, which is a divisional of 08/101,669 filed on Aug. 2, 1993 (now abandoned), which is a continuation of 07/834,735 filed Feb. 13, 1992 (now abandoned), which is a divisional of 07,504,785 filed Apr. 3, 1990 (now abandoned), which application(s) is(are) incorporated herein by reference and to which application(s) priority is claimed under 35 USC§ 120.

FIELD OF THE INVENTION

This invention relates to methods for the use of the Human Immunodeficiency Virus, or HIV, envelope (env) polypeptides, especially the preparation and use of HIV env variants and antibodies to HIV env, in the vaccination and treatment of HIV-infected patients.

BACKGROUND OF THE INVENTION

Acquired immunodeficiency syndrome (AIDS) is caused by a retrovirus identified as the human immunodeficiency virus (HIV). A number of immunologic abnormalities have been described in AIDS including abnormalities in B-cell function, abnormal antibody response, defective monocyte cell function, impaired cytokine production, depressed natural killer and cytotoxic cell function, and defective ability of lymphocytes to recognize and respond to soluble antigens. Other immunologic abnormalities associated with AIDS have been reported. Among the more important immunologic defects in patients with AIDS is the depletion of the T4 helper/inducer lymphocyte population.

In spite of the profound immunodeficiency observed in AIDS, the mechanism(s) responsible for immunodeficiency are not clearly understood. Several postulates exist. One accepted view is that defects in immune responsiveness are due to selective infection of helper T cells by HIV resulting in impairment of helper T-cell function and eventual depletion of cells necessary for a normal immune response. In vitro and in vivo studies showed that HIV can also infect monocytes which are known to play an essential role as accessory cells in the immune response. HIV may also result in immunodeficiency by interfering with normal cytokine production in an infected cell resulting in secondary immunodeficiency as for example, IL-1 and IL-2 deficiency. An additional means of HIV-induced immunodeficiency consists of the production of factors which are capable of suppressing the immune response. None of these models resolves the question of whether a component of HIV per se, rather than infection by replicative virus, is responsible for the immunologic abnormalities associated with AIDS.

The HIV env protein has been extensively described, and the amino acid and RNA sequences encoding HIV env from a number of HIV strains are known (Modrow, S. et al., *J. Virology* 61(2): 570 (1987). The HIV virion is covered by a membrane or envelope derived from the outer membrane of host cells. The membrane contains a population of envelope glycoproteins (gp 160) anchored in the membrane bilayer at their carboxyl terminal region. Each glycoprotein contains two segments. The N-terminal segment, called gp120 by virtue of its relative molecular weight of about 120 kD, protrudes into the aqueous environment surrounding the virion. The C-terminal segment, called gp41, spans the membrane. gp120 and gp 41 are covalently linked by a peptide bond that is particularly susceptible to proteolytic cleavage, see e.g. McCune et al., *EPO Application No.* 0 335 635, priority 28 Mar., 1988 and references cited therein.

Several approaches to an AIDS vaccine have been proposed, including inactivated and attenuated virus vaccines, subunit vaccines from virus-infected cells, recombinantly produced viral antigens, vaccines based on synthetic peptides, anti-idiotypic vaccines, and viral carrier-based vaccines, however no vaccination study published to date has provided protection against challenge with virus. Several reviews of HIV vaccine development have been published, e.g. Lasky, *Critical Reviews in Immunology* 9(3): 153–172 (1989), Newmark, *Nature* 333:699 (23 Jun. 23, 1988), and Fauci et al., *Annals of Internal Medicine* 110(5): 41–50 (1 Mar., 1989).

The use of whole (killed or attenuated) virus presents several problems, including the safety to workers producing the vaccine, and risk to those inoculated from incomplete inactivation of virus, or reversion of an attenuated virus to an active, virulent form. Both peptide and subunit vaccines could potentially have difficulty in obtaining their native conformations, and may only elicit humoral responses, perhaps not eliciting cell-mediated immunity. Another key difficulty in developing an AIDS vaccine lies in the variability of HIV from strain to strain, as well as in the same strain over time.

Of the proteins encoded by the HIV genome, the molecules most frequently used for vaccine development are located on the surface of the virus. They mediate virus attachment and the spread of the virus by cell-to-cell fusion (syncytia formation) and are the viral proteins most accessible to immune attack. Currently, gp120 is considered to be the best candidate for a subunit vaccine, because: (i) gp120 is known to possess the CD4 binding domain by which HIV attaches to its target cells, (ii) HIV infectivity can be neutralized in vitro by antibodies to gp 120, (iii) the majority of the in vitro neutralizing activity present in the serum of HIV infected individuals can be removed with a gp120 affinity column, and (iv) the gp 120/gp41 complex appears to be essential for the transmission of HIV by cell-to-cell fusion.

Vaccination of animals of several species with recombinant vectors that express HIV env are described in the literature. These vaccination attempts elicited strain-specific humoral immune responses as well as cell-mediated responses (see e.g. Van Eendenburg et al., *AIDS Research and Human Retroviruses* 5(1):41–50 (1989); Hu et al., *Nature* 320:537–540 (1986), Chakrabarti et al., *Nature* 320:535–537 (1986); Zarling et al., *Nature* 323:344–346 (1986); Hu et al., *Nature* 328:721–724 (1987); Zagury et al., *Nature* 326:249–250 (1987); Zagury et al., *Nature* 322:728–731 (1988).

Chimpanzees are the only nonhuman primate infectable with HIV and therefore they are the closest-to-human animal model system for vaccine-challenge study. Despite the promise suggested by the immune responses discussed above, published vaccine studies have all failed to protect chimpanzees from infection by HIV (see e.g. Hu et al., *Nature* 328:721–724 (1987) (vaccinia virus-HIV env recombinant vaccine); Arthur et al., *J. Virol.* 63(12): 5046–5053 (1989) (purified gp120); Berman et al., *Proc. Natl. Acad. Sci. USA* 85:5200–5204 (1988) (recombinant envelope glycoprotein gp120); and Prince et al., *Proc. Natl. Acad. Sci. USA* 85:6944–6948 (1988) (purified human HIV immune globulin).

The Simian Immunodeficiency Virus (SIV) is a lentivirus which is indigenous to healthy African monkeys; SIV is the animal lentivirus most closely related to HIV. Letvin el al., *Vaccines* 87, Cold Spring Harbor Lab 209–213 (1987)

discloses an unsuccessful attempt to immunize macaque monkeys against SIV using an inactivated virus vaccine. Desrosiers et al., *Proc. Natl. Acad. Sci. USA* 86:6353–6357 (1989) reported protection of two of six macaque monkeys against SIV by immunization with a detergent-disrupted whole virus SIV vaccine. Murphey-Corb et al., *Science* 246:1293–1297 (1989) disclose protection of eight of nine rhesus macaques against a SIV challenge by vaccination with a formalin-inactivated SIV whole virus vaccine.

It is therefore an object of this invention to provide vaccines capable of eliciting a protective immune response against HIV infection.

It is a further object of this invention to provide methods for preparing such HIV vaccines, and appropriate immunization schedules for the prevention and treatment of AIDS.

Other objects, features, and characteristics of the present invention will become apparent upon consideration of the following description and the appended claims.

SUMMARY OF THE INVENTION

The objects of this invention are accomplished by the preparation and administration an HIV antigen preparation which is suitable for administration to a human or non-human primate patient having or at risk of having HIV infection, in an amount and according to an immunization schedule sufficient to induce a protective immune response against HIV.

The vaccines of this invention may be administered alone or in combination with other HIV antigens, and in one or several immunization doses. Preferred immunization schedules are described, which generally provide for infrequent immunizations spaced at relatively long intervals, particularly a series of three or more inoculations administered over a period of one to two or more years.

This invention is particularly directed to vaccines comprising the HIV env polypeptides gp 120 and/or gp 160 which have a proteolytic clip site but have not been proteolytically cleaved at that internal clip site. This clip site of HIV env is believed to be located between amino acid residues 315–316 of the gp120 of the HIV strain described in EP 187,041A, commonly known as IIIB, or the equivalent region of other HIV strains.

HIV env preparations which are devoid of material containing the internal clip site are useful in vaccines for immunization against HIV infection. This unclipped HIV env polypeptide, including variant analogues thereof, is also useful in diagnostic assays for HIV neutralizing antibody in patient samples.

Methods of preparation of unclipped gp120 and gp160 are provided. In some embodiments, fermentation processes are provided, comprising expression of gp120 in mammalian cell culture, grown in media which has reduced or absent fetal calf or bovine serum; these fermentation methods encourage expression ad recovery of unclipped HIV env polypeptides. Methods of preparation of the vaccines of this invention are also disclosed.

Monoclonal antibodies are provided which are characterized by their affinity for ligand, epitope binding, and ability to a) block CD4/gp120 binding, b) neutralize HIV virions, c) reduce reverse transcriptase activity in vitro, and d) inhibit syncitia formation. In particular embodiments, monoclonal antibodies are provided that are specific for the region of gp120 which contains the internal clip site. These antibodies are useful as diagnostics for the presence of HIV infection in a patient or patient sample, and for affinity purification of unclipped gp120 or gp160. These antibodies are also useful in passively immunizing patients infected with HIV.

Antibodies directed to epitopes which span this clip site have been described in the literature; however, it should be noted that, due to the variety and confusion among authors currently as to numbering systems for HIV env sequences, not all antibodies described in the literature as directed to regions including amino acids 315–316 will actually span the clip site defined herein (see e.g. Matsushita et al., *J. Virol.* 62:2107–2114 (1988); EPO Application No. EP 339 504; Rusche et al., *Proc. Natl. Acad. Sci. USA*, 85:3198–3202 (1988); Looney et al., Science 241:357–359 (1988);

In certain embodiments, antibodies are provided which are capable of at least partially blocking the bonding of recombinant gp 120 to the T4 cell surface marker CD4. In other embodiments, antibody is provided which is at least partially capable of blocking syncytia formation between HIV-infected and uninfected cells and/or blocking reverse transcriptase activity. Brief Description of the Drawings FIG. 1 is a schematic representation of gp 120 showing disulfides and glycosylation sites. Roman numerals label the five disulfide-bonded domains. The five hypervariable regions of Modrow et al., *J. Virol.* 61:570–578 (1987) are enclosed in boxes and labelled V1–V5. Glycosylation sites containing high mannose-type and/or hybrid-type oligosaccharide structures are indicated by a branching-Y symbol, and glycosylation sites containing complex-type oligosaccharide structures are indicated by a V-shaped symbol. The clip site is designated by an arrow.

FIG. 2A and 2B show the amino acid sequences of FIG. 2A the mature HIV env glycoprotein gp120 from the IIIB isolate of HIV-1, and FIG. 2B the N-terminal sequence portion of the recombinant fusion glycoproteins (9AA or CL44) from the herpes simplex virus protein gD1. Fusion sites between the gD1 and gp120 segments in the 9AA and CL44 constructions are marked with (*) and (**), respectively. The letter T refers to observed tryptic cleavage of the gp 120 segment, and the peptides are ordered sequentially starting at the N-terminus of the molecule. Lower case letters following the T number indicate other unexpected proteolytic cleavages. The letter H refers to the observed tryptic cleavage of the herpes simplex gD1 protein portion of CL44. Peptide T2' contains the fusion site in CL44. The cysteine residues of gp120 are shaded, and potential N-linked glycosylation sites are indicated with a dot above the corresponding Asn residue.

FIG. 3A and 3B depict the composition of rgp120 and sgp160 immunogens used in the vaccination described in Example 1.

FIG. 3A is a schematic representation of the HIV-1 glycoprotein precursor, gp160, and the two variant gp160 derived proteins, rgp120, and sgp160, used in the present study. Both proteins differ at the amino terminus from wild-type gp160. In the rgp120 protein, the signal sequence and 31 residues of gp160 have been replaced with the signal sequence and 25 amino acids from the mature N-terminus of herpes simplex virus type 1 glycoprotein D (HSV-1 gD)[3]. In the sgp160 protein, the signal sequence and 12 amino acids of gp160 have been replaced with the signal sequence and 9 amino acids from the mature N-terminus of HSV-1 gD. In addition, the normal gp120/gp41 proteolytic processing site has been removed by a deletion spanning amino acid residues 502-511.

FIG. 3B depicts silver-stained SDS-PAGE gel of purified rgp120 and sgp160 under reducing and non-reducing conditions. Both recombinant glycoproteins were purified from growth conditioned cell culture supernatants by immunoaffinity chromatography and gel permeation chromatography to greater than 99% purity for rgp120 and greater than 95% purity for sgp160. Under non-reducing conditions the rgp120 contained less than 5% dimer while the sgp160 was approximately 50% dimer and higher order oligomers. Both proteins are subject to an endoproteolytic cleavage between arginine residue 315 and alanine residue 316 in the V3 region of the gp120 portion of each molecule. In rgp120 this results in the formation of an N-terminal 75 kD fragment and a 50 kD C-terminal fragment, while in sgp160 the same cleavage results in two fragments both of approximately 75 kD. On SDS-PAGE the fragments are visible only under reducing conditions because of disulfide bonding between cysteine residues 296 and 331. The rgp120 preparation contained less than 5% of the cleaved form whereas approximately 40% of the sgp160 was cleaved.

FIG. 5 is an autoradiograph showing analysis of ten monoclonal antibodies to sgp160. It can be seen that three major bands were specifically immunoprecipitated by one or more of the sera tested, a 140 kD band corresponding to sgp160, a 110–120 kD band corresponding to rgp120, and a 75 kD band which represents proteolytic breakdown products of gp120 and sgp160.

FIGS. 6A and 6B show the production of antibodies to rgp120 and sgp160 in animals immunized with candidate HIV-1 vaccines. Chimpanzees were immunized with 300 μg per dose of rgp160 (x-247 and x-261), rgp120 (x262 and x-265) or herpes simplex virus glycoprotein D (x-246), at times 0, 4 weeks, and 32 weeks (arrows). All immunogens were incorporated in aluminum hydroxide adjuvant containing 2 mg equivalents of $Al^{+3}$ per mg of protein. Blood was taken at the time points indicated, and the sera were analyzed for antibodies to rgp120 or sgp160 in the assays described for the in each of the specific panel descriptions. All animals were challenged by intravenous injection of 40 $TCID_{50}$ units of HIV-1 at 35 weeks. The open and closed squares represent the rgp120 immunized animals, x262 and x265, respectively. The open and closed circles represent the rsgp160 immunized animals, x247 and x261, respectively. The control animal, x246, is represented by the open triangles.

FIG. 6A illustrates detection of antibodies to rgp120 by immunoprecipitation of $^{125}I$-labeled rgp120 in a liquid phase radioimmunoprecipitation assay.

FIG. 6B shows detection of antibodies to HIV-1 proteins using a commercial (Genetic Systems) HIV-1 antibody assay kit (ELISA). Measurements were carried out according to the manufacturers instructions.

Figure 7:
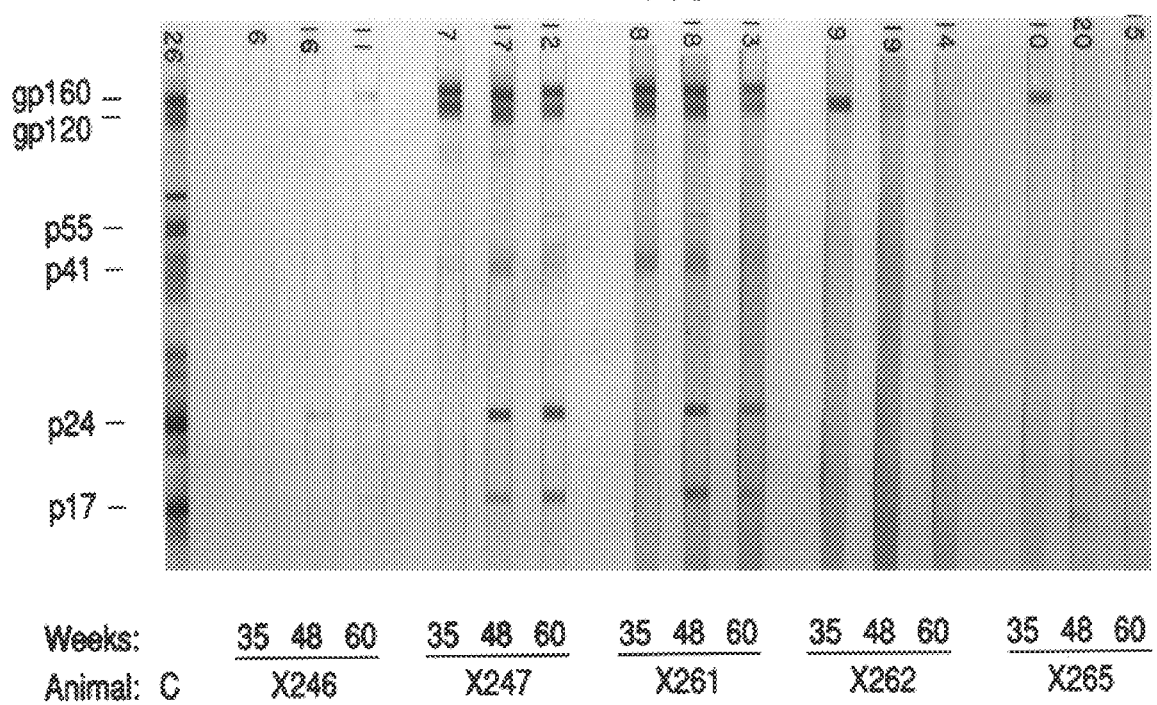

FIG. 7 shows immunoblot analysis of sera from animals immunized with candidate HIV-1 vaccines. Sera from chimpanzees immunized with sgp160 (x-247, x-261), rgp120 (x-262, x-265) or HSV-1 gD (x-246) were diluted and incubated with commercial (Dupont) immunoblot strips. The strips were incubated with alkaline phosphatase coupled goat anti-human IgG (Cappel) and developed with Phospharase substrate system obtained from Kirkegaard and Perry Laboratories. The data shown represent results obtained on the same day using the same lot of assay strips. Week 35 represents the time of challenge. The positive control consisted of serum from an HIV-1 infected individual.

Figure 8A:
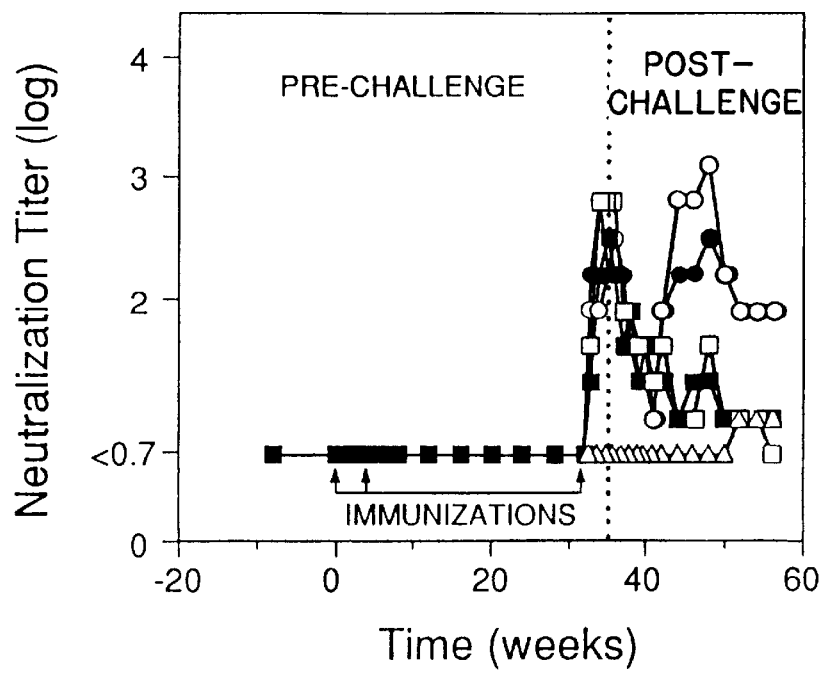
Figure 8B:
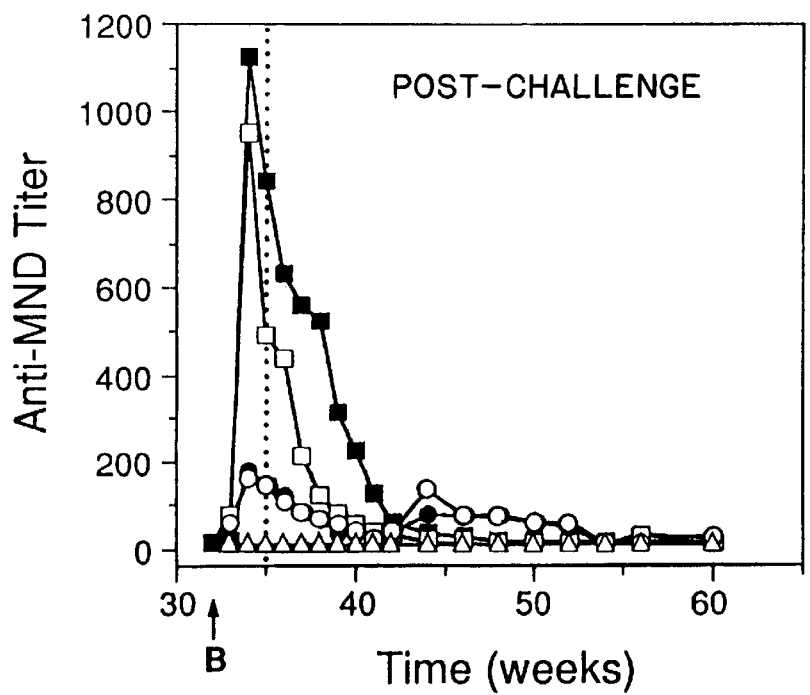

FIGS. 8A and 8B show antibodies that neutralize HIV-1 infectivity in vitro and bind to the major type specific neutralizing determinant (MND). Open and closed squares represent sera obtained from the rgp 120 immunized animals 262 and 265, respectively. The open and closed circles represent sera obtained from the rsgp160 immunized animals, 247 and 261, respectively. The open triangle represent the control animal (x246).

FIG. 8A shows the in vitro neutralizing activity in sera from chimpanzees immunized with rgp120 and sgp160 in a neutralization assay similar to that described by Robertson et al., J. Virol. Methods 20:195–202 (1988). Diluted samples of serum were incubated with 100 $TCID_{50}$ units of virus (IIIB isolate) for 60 minutes at 20° C. The mixture was transferred to cell culture plates containing $5\times10^4$ MT4 cells and incubated for 7 days. Virus lysis of infected cells was detected through the use of MTT as a vital stain. Neutralization assays were carried out in duplicate. Variation between replicates was less than one dilution (twofold). Sera from HIV-1 infected and uninfected chimpanzees were used as a positive and negative controls and gave neutralizing titers of 1:640 and <1:10 respectively.

FIG. 8B shows results of an ELISA assay to determine the relative concentration of antibodies reactive with the MND, where a synthetic peptide consisting of the sequence: NNTRKSIRKSIRIQRGPGRAFVTIGKIG and corresponding to amino acid residues 301 to 324 of gp120 from the IIIB isolate, was coated onto microtiter dish at a concentration of 2 μg per ml. After an overnight incubation at 40° C., the coated wells were washed with phosphate buffered saline (PBS) containing 0.05% Tween 20 and treated with a blocking buffer consisting of 0.8% bovine serum albumin in PBS. Each sample of chimpanzee sera serially diluted over a range of 1:10—to 1:10,240 and 100 p1 were incubated in the wells for 1.5 hr at room temperature. The wells were then washed four times with PBS containing 0.05% triton X-100. Labeled horseradish peroxidase conjugated goat-antihuman IgG was incubated for 1 hr and the plates washed four times with PBS, 0.05% Triton X-100. Antibody binding was indicated by a change in the color after the substrate o-phenylenediamine dihydrochloride was added. The colorometric reaction was stopped by the addition of 2.5M $H_2SO_4$, and the absorbance at 492 nm was measured in a plate reading spectrophotometer.

DETAILED DESCRIPTION OF THE INVENTION

HIV env is defined herein as the envelope polypeptide of Human Immunodeficiency Virus as described above, together with its amino acid sequence variants and derivatives produced by covalent modification of HIV env or its variants in vitro, as discussed herein. As used herein, the term "HIV env" encompasses all forms of gp120 and/or 160, e.g. including fragments, fusions of gp160/120 or their fragments with other peptides, and variantly glycosylated or unglycosylated HIV env. The HIV env of this invention is recovered free of active virus.

HIV env and its variants are conventionally prepared in recombinant cell culture. For example, see EP publication No. 187041. Henceforth, gp120 prepared in recombinant cell culture is referred to as rgp120. Recombinant synthesis is preferred for reasons of safety and economy, but it is known to prepare peptides by chemical synthesis and to purify HIV env from viral culture; such env preparations are included within the definition of HIV env herein.

Genes encoding HIV env are obtained from the genomic CDNA of an HIV strain or from available subgenomic clones containing the gene encoding HIV env. Cell cultures encoding gp120 of this invention have been deposited with the ATCC.

This invention is directed to the HIV env polypeptides gp120 or gp160, and preferably gp120, which have an internal cleavage site referred to herein as the "clip site" but which are not clipped at that site. These polypeptides are referred to herein as "unclipped HIV env", or more particularly "unclipped gp120" or "unclipped gp160". The clip site is a basic or dibasic residue susceptible to proteolytic cleavage.

As used herein, the term "clip site" does not refer to the cleavage site bridging gp120 and gp41, but instead refers to a proteolytic clip site which is located in gp 120 of HTLV-IIIB between Arg-Ala or Arg-Val residues, or between similarly situated residues in HIV strains currently common in the United States and in Africa, and in SIV strains. See Stephens et al., Nature 343:219 (1990).

Figure 1:
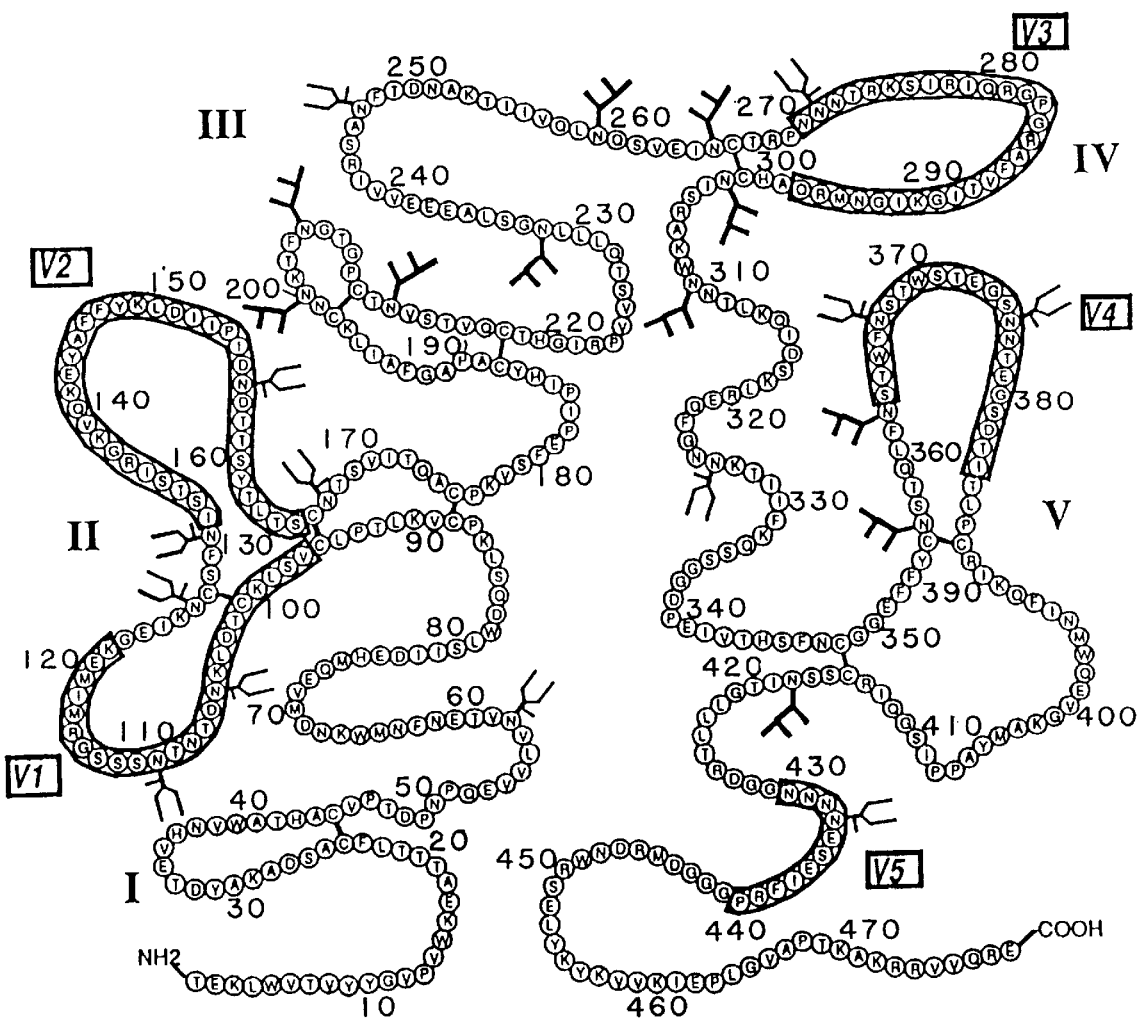

As shown by the arrow in FIG. 1, the clip site is located between amino acid residues 285–286 of the mature HIV-1 gp120 amino acid sequence, not counting any signal sequence or other upstream regions. For gp120 sequences which include the native HIV-IIIB N-terminal signal sequence, the clip site is found between residues 315–316; this numbering is used throughout this description to conveniently connote the residues at which the clip site is located, however it is understood that this invention is not limited to clip sites at those specific residue numbers. The same nucleotide and amino acid residue numbers may not be applicable in other strains where upstream deletions or insertions change the length of the viral genome and HIV env, but the region encoding this portion of gp120 is readily identified by reference to the teachings herein. Also, variant signal sequences (such as those resulting from a fusion with a fragmented or heterologous signal sequence as discussed below may lead to a slightly different numbering, however the location of the clip site is discerned for all embodiments by reference to the location of the arrow indicated in FIG. 1.

Included within the scope of unclipped HIV env as that term is used herein are HIV envs having the amino acid sequences set forth in FIG. 1 or 2, deglycosylated or unglycosylated derivatives of unclipped HIV env, homologous amino acid sequence variants of the sequence of FIG. 1 or 2, and homologous in vitro-generated variants and derivatives of unclipped HIV env, provided that all such variations do not interfere with the clip site, and which variants are capable of exhibiting a biological activity in common with the HIV env of FIG. 1 or FIG. 2.

Clipped or unclipped HIV env or HIV env-fragment biological activity is defined as either 1) immunological cross-reactivity with at least one epitope of clipped or unclipped HIV env, or 2) the possession of at least one adhesive or effector function qualitatively in common with clipped or unclipped HIV env. Examples of the qualitative biological activities of the HIV env include the ability of gp120 to bind to the viral receptor CD4, and the ability of gp120 to interact with gp41 to induce fusion of the viral and host cell membranes.

Immunologically cross-reactive as used herein means that the candidate polypeptide is capable of competitively inhibiting the qualitative biological activity of clipped or unclipped HIV env having this activity with polyclonal antisera raised against the known active analogue. Such antisera are prepared in conventional fashion by injecting goats or rabbits, for example, subcutaneously with the known active analogue in complete Freund's adjuvant, followed by booster intraperitoneal or subcutaneous injection in incomplete Freunds.

It is currently preferred that the unclipped HIV env preparations of this invention be substantially free of clipped HIV env fragments. By substantially free it is meant that the preparations should be greater than 50 percent, more preferably 60–70 percent, still more preferably 80 percent, and most preferably at least 90 percent free of clipped HIV env fragments.

The gp120 molecule consists of a polypeptide core of 60,000 daltons; extensive modification by N-linked glycosylation increases the apparent molecular weight of the molecule to 120,000 (Lasky et al., Science 233:209–212 (1986)). The amino acid sequence of gp120 contains five relatively conserved domains interspersed with five hypervariable domains (Modrow, supra). The hypervariable domains contain extensive amino acid substitutions, insertions and deletions. Sequence variations in these domains result in up to 25% overall sequence variability between gp120 molecules from the various viral isolates. Despite this variation, several structural and functional elements of gp120 are highly conserved. Among these are the ability of gp120 to bind to the viral receptor CD4, the ability of gp120 to interact with gp41 to induce fusion of the viral and host cell membranes, the positions of the 18 cysteine residues in the gp120 primary sequence, and the positions of 13 of the approximately 23 N-linked glycosylation sites in the gp120 sequence.

The ordinarily skilled worker may use the disulfide bonding pattern within gp120 and the positions of actual oligosaccharide moieties on the molecule for directing mutagenesis and fragmentation variants. It is intended that the variants of this invention include unclipped HIV env in which one or more residues—other than those at the clip site—have been substituted in the env amino acid sequence, deletions of one or more residues in the env sequence other than the clip site, and insertions of one or more residues adjacent to any residues except within the clip site.

Lasky et al., Science 233:209–212 (1986) described the expression of gp120 in Chinese hamster ovary (CHO) cells as a fusion protein using the signal peptide of the herpes simplex type 1 glycoprotein D(gD1). The use of two such fusions proteins are preferred in the practice of this invention. A recombinant glycoprotein (CL44) is expressed as a 498-amino acid fusion protein containing the first 27 residues of gD1 fused to residues 31–501 of gp120. This construction lacks the first cysteine residue of mature gp120. Another preferred recombinant fusion protein (9AA) contains the first 9 residues of gD1 fused to residues 4–501 of gp120. This restores the first cysteine residue, Cys24. Carboxy-terminal analysis of CL44 using carboxypeptidase digestions indicate that glutamic acid residue 479 is the carboxy terminus of the fully processed molecule secreted by CHO cells (data not shown). The amino acid sequences of these two constructions are given in FIG. 2.

This invention also contemplates amino acid sequence variants of the unclipped HIV env. Amino acid sequence variants are prepared with various objectives in mind, including increasing the affinity of the unclipped HIV env for a ligand or antibody, facilitating the stability, purification and preparation of the unclipped HIV env, modifying its plasma half life, improving therapeutic efficacy, and lessening the severity or occurrence of side effects during therapeutic use of the unclipped HIV env. In the discussion below, amino acid sequence variants of the unclipped HIV env are provided, exemplary of the variants that may be selected.

Amino acid sequence variants of unclipped HIV env fall into one or more of three classes: Insertional, substitutional, or deletional variants. These variants ordinarily are prepared by site-specific mutagenesis of nucleotides in the DNA encoding the unclipped HIV env, by which DNA encoding the variant is obtained, and thereafter expressing the DNA in recombinant cell culture. However, fragments having up to about 100–150 amino acid residues are prepared conveniently by in vitro synthesis. The following discussion applies to any unclipped HIV env to the extent it is applicable to its structure or function.

The amino acid sequence variants of the unclipped HIV env are predetermined variants not found in nature or naturally occurring alleles. The unclipped HIV env variants typically exhibit the same qualitative biological—for example, antibody binding—activity as the naturally occurring unclipped HIV env or unclipped HIV env analogue. However, unclipped HIV env variants and derivatives that are not capable of binding to antibodies are useful nonetheless (a) as a reagent in diagnostic assays for HIV env or antibodies to the HIV env, (b) when insolubilized in accord with known methods, as agents for purifying anti-unclipped HIV env antibodies from antisera or hybridoma culture supernatants, and (c) as immunogens for raising antibodies to unclipped HIV env or as immunoassay kit components (labelled, as a competitive reagent for the native HIV env or unlabelled as a standard for HIV env assay) so long as at least one HIV env epitope remains active.

While the site for introducing an amino acid sequence variation is predetermined, the mutation per se need not be predetermined. For example, in order to optimize the performance of a mutation at a given site, random or saturation mutagenesis (where all 20 possible residues are inserted) is conducted at the target codon and the expressed HIV env variant is screened for the optimal combination of desired activities. Such screening is within the ordinary skill in the art.

Amino acid insertions usually will be on the order of about from 1 to 10 amino acid residues; substitutions are typically introduced for single residues; and deletions will range about from 1 to 30 residues. Deletions or insertions preferably are made in adjacent pairs, i.e. a deletion of 2 residues or insertion of 2 residues. It will be amply apparent from the following discussion that substitutions, deletions, insertions or any combination thereof are introduced or combined to arrive at a final construct.

Insertional amino acid sequence variants of unclipped HIV env are those in which one or more amino acid residues extraneous to the HIV env are introduced into a predetermined site (other than at the clip site) in the target unclipped HIV env and which displace the preexisting residues.

Commonly, insertional variants are fusions of heterologous proteins or polypeptides to the amino or carboxyl terminus of the unclipped HIV env. Such variants are referred to as fusions of the unclipped HIV env and a polypeptide containing a sequence which is other than that which is normally found in the unclipped HIV env at the inserted position. Several groups of fusions are contemplated herein.

The novel polypeptides of this invention are useful in diagnostics or in purification of the antibodies or ligands by known immunoaffinity techniques.

Desirable fusions of unclipped HIV env, which may or may not also be immunologically active, include fusions of the mature unclipped HIV env sequence with a signal sequence heterologous to the binding partner as mentioned above. Signal sequence fusions are employed in order to more expeditiously direct the secretion of the unclipped HIV env. The heterologous signal replaces the native HIV env signal, and when the resulting fusion is recognized, i.e. processed and cleaved by the host cell, the unclipped HIV env is secreted. Signals are selected based on the intended host cell, and may include bacterial yeast, mammalian and viral sequences. The native HIV env signal or the herpes gD glycoprotein signal is suitable for use in mammalian expression systems.

C-terminal or N-terminal fusions of the unclipped HIV env or unclipped HIV env fragment with an immunogenic hapten or heterologous polypeptide are useful as vaccine components for the immunization of patients against HIV infection. Fusions of the hapten or heterologous polypeptide with unclipped HIV env or its active fragments which retain T-cell binding activity are also useful in directing cytotoxic T cells against target cells where the hapten or heterologous polypeptide is capable of binding to a target cell surface receptor. For example, membrane-bound transforming growth factor-α(TGF-α) is present on the surface of many solid (non-hematopoietic) neoplastic tumors. Antibodies capable of binding TGF-α are known, and may be linked to unclipped HIV env, e.g. by covalent crosslinking according to commonly known methods, or by expression in recombinant cell culture as an N- or C-terminal fusion with unclipped HIV env or active fragment, and are used to target unclipped gp120 to TGF-α.

The precise site at which the fusion is made is variable; particular HIV env sites are well known and may be selected in order to optimize the biological activity, secretion or binding characteristics of the unclipped HIV env. The optimal site will for a particular application will be determined by routine experimentation.

Substitutional variants are those in which at least one residue in the FIG. 1 or 2 sequence has been removed (other than those residues at the clip site) and a different residue inserted in its place. Such substitutions generally are made in accordance with the following Table 1 when it is desired to finely modulate the characteristics of the unclipped HIV env.

TABLE 1

| Original Residue | Exemplary Substitutions |
| --- | --- |
| Ala | ser |
| Arg | lys |
| Asn | gln; his |
| Asp | glu |
| Cys | ser; ala |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Novel amino acid sequences, as well as isosteric analogs (amino acid or otherwise), as included within the scope of this invention.

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in unclipped HIV env properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Some deletions, insertions, and substitutions will not produce radical changes in the characteristics of the unclipped HIV env molecule. However, when it is difficult to predict the exact effect of the substitution, deletion, or insertion in advance of doing so, for example when modifying an immune epitope, one skilled in the art will appreciate that the effect will be evaluated by routine screening assays. For example, a variant typically is made by site specific mutagenesis of the HIV env -encoding nucleic acid, expression of the variant nucleic acid in recombinant cell culture and, optionally, purification from the cell culture for example by immunoaffinity adsorption on a polyclonal anti-unclipped HIV env column (in order to adsorb the variant by at least one remaining immune epitope). The activity of the cell lysate or purified unclipped HIV env variant is then screened in a suitable screening assay for the desired characteristic. For example, a change in the immunological character of the unclipped HIV env, such as affinity for T-cell binding, measured by a competitive-type immunoassay. As more becomes known about the functions in vivo of the unclipped HIV env other assays will become useful in such screening. Modifications of such protein properties as redox or thermal stability, hydrophobicity, susceptibility to proteolytic degradation, or the tendency to aggregate with carriers or into multimers are assayed by methods well known to the artisan.

Another class of unclipped HIV env variants are deletional variants. Deletions are characterized by the removal of one or more amino acid residues (other than the clip site) from the HIV env sequence. Typically, deletions are used to affect unclipped HIV env biological activities, however, deletions which preserve the biological activity or immune cross-reactivity of the unclipped HIV env are suitable.

Deletions of cysteine or other labile residues also may be desirable, for example in increasing the oxidative stability of the unclipped HIV env. Deletion or substitutions of potential proteolysis sites, e.g. Arg Arg, is accomplished by deleting one of the basic residues or substituting one by glutaminyl or histidyl residues.

It will be understood that some variants may exhibit reduced or absent biological activity. These variants nonetheless are useful as standards in immunoassays for HIV env so long as they retain at least one immune epitope of HIV env.

It is presently believed that the three-dimensional structure of the unclipped HIV env compositions of the present invention is important to their functioning as described herein. Therefore, all related structural analogs which mimic the active structure of those formed by the compositions claimed herein are specifically included within the scope of the present invention.

Glycosylation variants are included within the scope of unclipped HIV env. They include variants completely lacking in glycosylation (unglycosylated) and variants having at least one less glycosylated site than the native form (deglycosylated) as well as variants in which the glycosylation has been changed. Included are deglycosylated and unglycosylated amino acid sequence variants, deglycosylated and unglycosylated unclipped HIV env having the native, unmodified amino acid sequence of HIV env, and other glycosylation variants. For example, substitutional or deletional mutagenesis is employed to eliminate the N-or O-linked glycosylation sites of unclipped HIV env, e.g., an asparagine residue (not at the clip site) is deleted or substituted for by another basic residue such as lysine or histidine. Alternatively, flanking residues making up the glycosylation site are substituted or deleted, even though the asparagine residues remain unchanged, in order to prevent glycosylation by eliminating the glycosylation recognition site.

Unglycosylated unclipped HIV env which has the amino acid sequence of the native HIV env is produced in recombinant prokaryotic cell culture because prokaryotes are incapable of introducing glycosylation into polypeptides.

Glycosylation variants are produced by selecting appropriate host cells or by in vitro methods. Yeast, for example, introduce glycosylation which varies significantly from that of mammalian systems. Similarly, mammalian cells having a different species (e.g. hamster, murine, insect, porcine, bovine or ovine) or tissue origin (e.g. lung, liver, lymphoid, mesenchymal or epidermal) than the source of the HIV env antigen are routinely screened for the ability to introduce variant glycosylation as characterized for example by elevated levels of mannose or variant ratios of mannose, fucose, sialic acid, and other sugars typically found in mammalian glycoproteins. In vitro processing of the unclipped HIV env typically is accomplished by enzymatic hydrolysis, e.g. neuraminidase digestion.

Covalent modifications of the unclipped HIV env molecule which do not modify the clip site are included within the scope hereof. Such modifications are introduced by reacting targeted amino acid residues of the recovered protein with an organic derivatizing agent that is capable of reacting with selected side chains or terminal residues, or by harnessing mechanisms of post-translational modification that function in selected recombinant host cells. The resulting covalent derivatives are useful in programs directed at identifying residues important for biological activity, for immunoassays of HIV env or for the preparation of anti-unclipped HIV env antibodies for immunoaffinity purification of the recombinant unclipped HIV env. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Derivatization with bifunctional agents is useful for preparing intermolecular aggregates of the unclipped HIV env with polypeptides as well as for cross-linking the unclipped HIV env to a water insoluble support matrix or surface for use in the assay or affinity purification of its ligands. In addition, a study of intrachain cross-links will provide direct information on conformational structure. Commonly used cross-linking agents include suflhydryl reagents, 1,1-bis (diazoacetyl)-2-phenylethane, glutaraldehyde, N-hydroxysuccinimideesters, for example esters with 4-azidosalicylic acid, homobifunctional imidoesters including disuccinimidyl esters such as 3,3'-dithiobis (succinimidyl-propionate), and bifunctional maleimides such as bis-N-maleimido- 1,8-octane. Derivatizing agents such as methyl-3-[(p-azido-phenyl)dithio] propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,080; 3,969,287; 3,691, 016; 4,195,128; 4,247,642; 4,229,537; 4,055,635; and 4,330,440 are employed for protein immobilization and cross-linking.

Polymers generally are covalently linked to the peptide herein through a multifunctional crosslinking agent which reacts with the polymer and one or more amino acid or sugar residues of protein. However, it is within the scope of this invention to directly crosslink the polymer by reacting a derivatized polymer with the peptide, or vice versa. Covalent bonding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylchloroformate or p-nitrophenylchloroformate activated PEG. Carboxyl groups are derivatized by coupling PEG-amine using carbodiimide.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco pp 79–86 [1983]), acetylation of the N-terminal amine and, in some instances, amidation of the C-terminal carboxyl.

DNA encoding unclipped HIV env is synthesized by in vitro methods or is obtained readily from cDNA libraries. The means for synthetic creation of the DNA encoding unclipped HIV env, either by hand or with an automated apparatus, are generally known to one of ordinary skill in the art, particularly in light of the teachings contained herein. As examples of the current state of the art relating to polynucleotide synthesis, one is directed to Maniatis et al., *Molecular Cloning—A Laboratory Manual,* Cold Spring Harbor Laboratory (1984), and Horvath et al., *An Automated DNA Synthesizer Employing Deoxynucleoside 3'-Phosphoramidites, Methods in Enzymology* 154: 313–326, 1987, hereby specifically incorporated by reference.

Alternatively, to obtain DNA encoding unclipped HIV env, one needs only to conduct hybridization screening with labelled DNA encoding either the HIV env or unclipped HIV env fragments thereof as shown in FIGS. 1 and 2 (usually, greater than about 20, and ordinarily about 50 bp) in order to detect clones which contain homologous sequences in the cDNA libraries derived from cells or tissues of a particular animal, followed by analyzing the clones by restriction enzyme analysis and nucleic acid sequencing to identify full-length clones. If full length clones are not present in the library, then appropriate fragments are recovered from the various clones and ligated at restriction sites common to the fragments to assemble a full-length clone. DNA encoding HIV env from various isotypes and strains is obtained by probing libraries from hosts of such species with the sequences of FIGS. 1 or 2, or by synthesizing the genes in vitro. DNA for other isotypes or strains having known sequences may be obtained with the use of analogous routine hybridization procedures.

In general, prokaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting. Alternatively, in vitro methods of cloning, e.g. polymerase chain reaction, are suitable.

The polypeptides of this invention are expressed directly in recombinant cell culture as an N-terminal methionyl analogue, or as a fusion with a polypeptide heterologous to the hybrid/portion, preferably a signal sequence or other polypeptide having a specific cleavage site at the N-terminus of the hybrid/portion. For example, in constructing a prokaryotic secretory expression vector for unclipped HIV env, the native HIV env signal is employed with hosts that recognize that signal. When the secretory leader is "recognized" by the host, the host signal peptidase is capable of cleaving a fusion of the leader polypeptide fused at its C-terminus to the desired mature unclipped HIV env. For host prokaryotes that do not process the HIV env signal, the signal is substituted by a prokaryotic signal selected for example from the group of the alkaline phosphatase, penicillinase, lpp or heat stable enterotoxin II leaders. For yeast secretion the HIV env signal may be substituted by the yeast invertase, alpha factor or acid phosphatase leaders. In mammalian cell expression the native signal is satisfactory for unclipped mammalian HIV env, although other mammalian secretory protein signals are suitable, as are viral secretory leaders, for example the herpes simplex gD signal.

Unclipped HIV env may be expressed in any host cell, but preferably is synthesized in mammalian hosts. However, host cells from prokaryotes, fungi, yeast, insects and the like are also are used for expression. Exemplary prokaryotes are the strains suitable for cloning as well as *E. coli* W3110 ($F^-$, $\lambda^-$, prototrophic, ATTC No. 27325), other enterobacteriaceae such as *Serratia marcescans,* bacilli and various pseudomonads. Preferably the host cell should secrete minimal amounts of proteolytic enzymes.

Expression hosts typically are transformed with DNA encoding the unclipped HIV env which has been ligated into an expression vector. Such vectors ordinarily carry a replication site (although this is not necessary where chromosomal integration will occur). Expression vectors also include marker sequences which are capable of providing phenotypic selection in transformed cells, as will be discussed further below. For example, *E. coli* is typically transformed using pBR322, a plasmid derived from an *E. coli* species (Bolivar, et al., Gene 2: 95 [1977]). pBR322 contains genes for ampicillin and tetracycline resistance and thus provides easy means for identifying transformed cells, whether for purposes of cloning or expression. Expression vectors also optimally will contain sequences which are useful for the control of transcription and translation, e.g., promoters and Shine-Dalgarno sequences (for prokaryotes) or promoters and enhancers (for mammalian cells). The promoters may be, but need not be, inducible; even powerful constitutive promoters such as the CMV promoter for mammalian hosts may produce unclipped HIV env without host cell toxicity. While it is conceivable that expression vectors need not contain any expression control, replicative sequences or selection genes, their absence may hamper the identification of transformants and the achievement of high level peptide expression.

Promoters suitable for use with prokaryotic hosts illustratively include the β-lactamase and lactose promoter systems (Chang et al., *Nature* 275: 615 [1978]; and Goeddel et al., *Nature* 281: 544 [1979]), alkaline phosphatase, the tryptophan (trp) promoter system (Goeddel, *Nucleic Acids Res.* 8: 4057 (1980) and EPO Appln. Publ. No. 36,776) and hybrid promoters such as the tac promoter (H. de Boer et al., *Proc. Natl. Acad. Sci. USA* 80: 21–25 [1983]). However, other functional bacterial promoters are suitable. Their nucleotide sequences are generally known, thereby enabling a skilled worker operably to ligate them to DNA encoding unclipped HIV env (Siebenlist et al., *Cell* 20: 269 [1980]) using linkers or adaptors to supply any required restriction sites. Promoters for use in bacterial systems also will contain a Shine-Dalgarno (S.D.) sequence operably linked to the DNA encoding the unclipped HIV env.

In addition to prokaryotes, eukaryotic microbes such as yeast or filamentous fungi are satisfactory. *Saccharomyces cerevisiae* is the most commonly used eukaryotic microorganism, although a number of other strains are commonly available. The plasmid YRp7 is a satisfactory expression vector in yeast (Stinchcomb, et al., *Nature* 282: 39 (1979); Kingsman et al, Gene 7: 141 (1979); Tschemper et al., *Gene* 10: 157 (1980)). This plasmid already contains the trp1 gene which provides a selection marker for a mutant strain of yeast lacking the ability to grow in tryptophan, for example ATCC no. 44076 or PEP4-1 (Jones, *Genetics* 85: 12 [1977]). The presence of the trp1 lesion as a characteristic of the yeast host cell genome then provides an effective environment for detecting transformation by growth in the absence of tryptophan.

Suitable promoting sequences for use with yeast hosts include the promoters for 3-phosphoglycerate kinase (Hitzeman et al. *J. Biol. Chem.* 255: 2073 (1980)) or other glycolytic enzymes (Hess et al., *J. Adv. Enzyme Reg.* 7: 149 (1968); and Holland, *Biochemistry* 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A.

Expression control sequences are known for eucaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the coding sequence. All of these sequences are inserted into mammalian expression vectors.

Suitable promoters for controlling transcription from vectors in mammalian host cells are readily obtained from various sources, for example, the genomes of viruses such as polyoma virus, SV40, adenovirus, MMV (steroid inducible), retroviruses (e.g. the LTR of HIV), hepatitis-B virus and most preferably cytomegalovirus, or from heterologous mammalian promoters, e.g. the beta actin promoter. The early and late promoters of SV40 are conveniently obtained as an SV40 restriction fragment which also contains the SV40 viral origin of replication. Fiers et al., *Nature,* 273: 113 (1978). The immediate early promoter of the human cytomegalovirus is conveniently obtained as a HindIII E restriction fragment. Greenaway, P. J. et al., *Gene* 18: 355–360 (1982).

Transcription of a DNA encoding unclipped HIV env by higher eukaryotes is increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., PNAS 78: 993 [1981]) and 3' (Lusky, M. L., et al., *Mol. Cell Bio.* 3: 1108 (1983)) to the transcription unit, within an intron (Banerji, J. L. et al. *Cell* 33: 729 (1983)) as well as within the coding sequence itself (Osborne, T. F., et al., *Mol. Cell Bio.* 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding the hybrid immunoglobulin. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase (TK) or neomycin. When such selectable markers are successfully transferred into a mammalian host cell, the transformed mammalian host cell is able to survive if placed under selective pressure. There are two widely used distinct categories of selective regimes. The first category is based on a cell's metabolism and the use of a mutant cell line which lacks the ability to grow independent of a supplemented media. Two examples are CHO $DHFR^-$ cells and mouse $LTK^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media. In preferred embodiments, herein, CHO cells which are DHFR⁺ are used for recombinant expression of gp120.

The second category of selective regimes is dominant selection which refers to a selection scheme used in any cell type and does not require the use of a mutant cell line. These schemes typically use a drug to arrest growth of a host cell. Those cells which are successfully transformed with a heterologous gene express a protein conferring drug resistance and thus survive the selection regimen. Examples of such dominant selection use the drugs neomycin (Southern et al., *J. Molec. Appl. Genet.* 1: 327 (1982)), mycophenolic acid (Mulligan et al., *Science* 209: 1422 (1980)) or hygromycin (Sugden et al., *Mol. Cell. Biol.* 5: 410–413 (1985)). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent, e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and teh DHFR or amplification gene permitting cointegration. One ensures that the cell requires more DHFR, which requirement is met by replication of teh selection gene, by selecting only for cells that can grow in teh presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired protein.

Suitable eukaryotic host cells for expressing unclipped HIV env include monkey kidney CV1 line transformed by SV40 (COS-7, ATCC CRL 1651); human embryonic kidney line (293 or 293 cells subcloned for growth in suspension culture, Graham, F. L. et al., *J. Gen Virol.* 36: 59 (1977)); baby hamster kidney cells (BHK, ATCC CCL 10); chinese hamster ovary-cells-DHFR (CHO, Urlaub and Chasin, PNAS (USA) 77: 4216, [1980]); mouse sertoli cells (TM4, Mather, J. P., Biol. Reprod. 23: 243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, J.P. et al., *Annals N.Y. Acad. Sci.* 383: 44–68 [1982]).

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform *E. coli* K12 strain 294 (ATCC 31446) and successful transformants selected by ampicillin or tetracycline resistance where appropriate. Plasmids from the transformants are prepared, analyzed by restriction and/or sequenced by the method of Messing et al., *Nucleic Acids Res.* 9: 309 (1981) or by the method of Maxam et al., *Methods in Enzymology* 65: 499 (1980).

Host cells are transformed with the expression vectors of this invention and cultured in conventional nutrient media modified as appropriate for inducing promoters, selecting transformants or amplifying the genes encoding the desired sequences. The culture conditions, such as temperature, pH and the like, are those previously used with the host cell selected for expression, and will be apparent to the ordinarily skilled artisan.

To maximize the harvest of unclipped HIV env, it is currently preferred that cell cultures be grown in media containing low serum, preferably 0–3 percent serum, and more preferably in about 1 percent fetal bovine serum or other suitable serum.

The host cells referred to in this disclosure encompass cells in in vitro culture as well as cells which are within a host animal.

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., *Virology* 52: 456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., *Proc. Natl. Acad. Sci. (USA),* 69: 2110 (1972).

"Transfection" refers to the introduction of DNA into a host cell whether or not any coding sequences are ultimately expressed. Numerous methods of transfection are known to the ordinarily skilled artisan, for example, $CaPO_4$ and electroporation. Transformation of the host cell is the indicia of successful transfection.

The novel polypeptide of this invention is recovered and purified from recombinant cell cultures by known methods, including ammonium sulfate or ethanol precipitation, acid extraction, anion or cation exchange chromatography, phosphocellulose chromatography, immunoaffinity chromatography, hydroxyapatite chromatography and lectin chromatography. See, e.g., the purification methods described in EP 187,041. Moreover, reverse-phase HPLC and chromatography using ligands for unclipped HIV env are useful for purification. It is presently preferred to utilize gel permeation chromatography and anion exchange chromatography, and more preferred to use cation exchange and hydrophobic interaction chromatography (HIC) according to standard protocols.

Additionally, unclipped HIV env is recovered and purified by passage over a column of unclipped HIV env-antibody covalently coupled to aldehyde silica by a standard procedure (Roy et al., *Journal of Chromatography* 303:225–228 (1984)), washing of the column with a saline solution, and analyzing the eluant by standard methods such as quantitative amino acid analysis. Procedures utilizing monoclonal antibodies coupled to glycerol-coated controlled pore glass are desirable for the practice of this invention. Optionally, low concentrations (approximately 1–5 mM) of calcium ion may be present during purification. Unclipped HIV env may preferably be purified in the presence of a protease inhibitor such as PMSF.

Unclipped HIV env is placed into pharmaceutically acceptable, sterile, isotonic formulations together with required cofactors, and optionally are administered by standard means well known in the field. The formulation is preferably liquid, and is ordinarily a physiologic salt solution containing non-phosphate buffer at pH 6.8–7.6, or may be lyophilized powder.

The unclipped HIV env compositions to be used in the therapy will be formulated and dosages established in a fashion consistent with good medical practice taking into account the disorder to be treated, the condition of the individual patient, the site of delivery of the unclipped HIV env polypeptide, the method of administration and other factors known to practitioners.

Unclipped HIV env is prepared for administration by mixing unclipped HIV env at the desired degree of purity with adjuvants or physiologically acceptable carriers i.e. carriers which are nontoxic to recipients at the dosages and concentrations employed. Adjuvants and carriers are substances that in themselves share no immune epitopes with the target antigen, but which stimulate the immune response to the target antigen. Ordinarily, this will entail combining unclipped HIV env with buffers, low molecular weight (less that about 10 residues) polypeptides, proteins, amino acids, carbohydrates including glucose or dextrans, chelating agents such as EDTA, and other excipients. Freunds adjuvant (a mineral oil emulsion) commonly has been used for this purpose, as have a variety of toxic microbial substances such as mycobacterial extracts and cytokines such as tumor necrosis factor and interferon gamma (described in co-pending U.S. Ser. No. 07/007075). Although antigen is desirably administered with an adjuvant, in sitatuions where the initial inoculation is delivered with an adjuvant, boosters with antigen may not require adjuvant. Carriers often act as adjuvants, but are generally distinguished from adjuvants in that carriers comprise water insoluble macromolecular particulate structures which aggregate the antigen, Typical carriers include aluminum hydroxide, latex particles, bentonite and liposomes.

It is envisioned that injections (intramuscular or subcutaneous) will be the primary route for therapeutic administration of the vaccines of this invention, intravenous delivery, or delivery through catheter or other surgical tubing is also used. Alternative routes include tablets and the like, commercially available nebulizers for liquid formulations, and inhalation of lyophilized or aerosolized receptors. Liquid formulations may be utilized after reconstitution from powder formulations.

The novel polypeptide may also be administered via microspheres, liposomes, other microparticulate delivery systems or sustained release formulations placed in certain tissues including blood. Suitable examples of sustained release carriers include semipermeable polymer matrices in the form of shaped articles, e.g. suppositories, or microcapsules. Implantable or microcapsular sustained release matrices include polylactides (U.S. Pat. No. 3,773,919, EP 58,481) copolymers of L-glutamic acid and gamma ethyl-L-glutamate (U. Sidman et al., *Biopolymers* 22(1): 547–556, (1985)), poly (2-hydroxyethyl-methacrylate) or ethylene vinyl acetate (R. Langer et al., *J. Biomed. Mater. Res.* 15: 167–277 (1981) and R. Langer, *Chem. Tech.* 12: 98–105 (1982)). Liposomes containing the unclipped HIV env are prepared by well-known methods: DE 3,218,121A; Epstein et al., *Proc. Nail. Acad. Sci. USA*, 82:3688–3692 (1985); Hwang et al., *Proc. Natl. Acad. Sci. USA*, 77:4030–4034 (1980); EP 52322A; EP 36676A; EP 88046A; EP 143949A; EP 142541A; Japanese patent application 83-11808; U.S. Pat. Nos. 4,485,045 and 4,544,545; and UP 102,342A. Ordinarily the liposomes are of the small (about 200–800 Angstroms) unilamelar type in which the lipid content is greater than about 30 mol. % cholesterol, the selected proportion being adjusted for the optimal rate of the polypeptide leakage.

The vaccination dose of the unclipped HIV env administered will be dependent upon the properties of the vaccine employed, e.g. its binding activity and in vivo plasma half-life, the concentration of the unclipped HIV env in the formulation, the administration route, the site and rate of dosage, the clinical tolerance of the patient involved, the pathological condition afflicting the patient and the like, as is well within the skill of the physician. Generally, doses of 300 $\mu$g of unclipped HIV env per patient per administration are preferred, although dosages may range from about 10 $\mu$g–1 mg per dose. Different dosages are utilized during a series of sequential inoculations; the practitioner may administer an initial inoculation and then boost with relatively smaller doses of unclipped HIV env vaccine.

The unclipped HIV env vaccines of this invention may be administered in a variety of ways and to different classes of recipients. The vaccines are used to vaccinate individuals who may or may not be at risk of exposure to HIV, and additionally, the vaccines are desirably administered to seropositive individuals and to individuals who have been previously exposed to HIV (see e.g. Salk, *Nature* 327:473–476 (1987); and Salk et al., *Science* 195:834–847 (1977)).

The unclipped HIV env may be administered in combination with other antigens in a single inoculation "cocktail". The unclipped HIV env vaccines may also be administered as one of a series of inoculations administered over time. Such a series may include inoculation with the same or different preparations of HIV antigens or other vaccines.

The adequacy of the vaccination parameters chosen, e.g. dose, schedule, adjuvant choice and the like, is determined by taking aliquots of serum from the patient and assaying antibody titers during the course of the immunization program. Alternatively, the presence of T cells may by monitored by conventional methods as described in Example 1 below. In addition, the clinical condition of the patient will be monitored for the desired effect, e.g. anti-infective effect. If inadequate vaccination is achieved then the patient can be boosted with further unclipped HIV env vaccinations and the vaccination parameters can be modified in a fashion expected to potentiate the immune response, e.g. increase the amount of antigen and/or adjuvant, complex the antigen with a carrier or conjugate it to an immunogenic protein, or vary the route of administration.

This invention is also directed to optimized immunization schedules for enhancing a protective immune response against HIV infection. It is currently preferred that at least three separate inoculations with unclipped HIV env be administered, with a second inoculation being administered more than two, preferably three to eight, and more preferably approximately four weeks following the first inoculation. It is preferred that a third inoculation be administered several months later than the second "boost" inoculation, preferably at least more than five months following the first inoculation, more preferably six months to two years following the first inoculation, and even more preferably eight months to one year following the first inoculation. Periodic inoculations beyond the third are also desirable to enhance the patient's "immune memory". See Anderson et al., *J. Infectious Diseases* 160(6):960–969 (Dec. 1989) and the references therein, incorporated by reference herein. Generally, infrequent immunizations with unclipped HIV env spaced at relatively long intervals is more preferred than frequent immunizations in eliciting maximum antibody responses, and in eliciting a protective effect.

The polypeptides of this invention may optionally be administered along with other pharmacologic agents used to treat AIDS or ARC or other HIV-related diseases and infections, such as AZT, CD4, antibiotics, immunomodulators such as interferon, anti-inflammatory agents, and anti-tumor agents.

Antibodies

This invention is also directed to monoclonal antibodies, as illustrated in Example 2 below and by antibody hybridomas deposited with the ATCC (as described below). In accordance with this invention, monoclonal antibodies specifically binding an epitope of unclipped HIV env or antigenically active, cell surface-exposed fragments thereof (for example epitopes chosen from gp120, gp41) are isolated from continuous hybrid cell lines formed by the fusion of antigen-primed immune lymphocytes with myeloma cells. Advantageously, the monoclonal antibodies of the subject invention which bind HIV env and unclipped HIV env bind the domain of this protein which is exposed on the cell surface.

The antibodies of the subject invention are obtained through routine screening. An assay is used for screening monoclonal antibodies for their cytotoxic potential as ricin A chain containing immunotoxins. The assay involves treating cells with dilutions of the test antibody followed by a Fab fragment of a secondary antibody coupled to ricin A chain ('indirect assay'). The cytotoxicity of the indirect assay is compared to that of the direct assay where the monoclonal antibody is coupled to ricin A chain. The indirect assay accurately predicts the potency of a given monoclonal antibody as an immunotoxin and is thus useful in screening monoclonal antibodies for use as immunotoxins-see also Vitetta et al., *Science* 238:1098–1104 (1987), and Weltman et al., *Cancer Res.* 47:5552 (1987), hereby incorporated by reference.

Monoclonal antibodies are highly specific, being directed against a single antigenic site. Furthermore, in contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. A second advantage of monoclonal antibodies is that they are synthesized by the hybridoma culture, uncontaminated by other immunoglobulins. Monoclonal antibodies may be prepared from supernatants of cultured hybridoma cells or from ascites induced by intra-peritoneal inoculation of hybridoma cells into mice.

The hybridoma technique described originally by Kohler and Milstein, *Eur. J. Immunol.*, 6:511 (1976) has been widely applied to produce hybrid cell lines that secrete high levels of monoclonal antibodies against many specific antigens.

In particular embodiments of this invention, an antibody capable of blocking or binding to an epitope spanning the gp120 proteolytic clip site is obtained by immunizing mice such as Balb/c or, preferably C57 BL/6, against gp120 and screening for a clonal antibody that, when preincubated with unclipped gp120, prevents its binding to clipped gp120. The 10F6, 11G5, and 10D8 antibodies are examples of such an antibody, but they are not unique since other antibodies having the same qualitative activity can be obtained by the method described herein, and as described above, antibodies which span the clip site are known in the literature. "Qualitative" activity in this context means that the antibody binds to an epitope spanning the clip site of HIV env. A tryptic digest of gp120 showed that the 10F6, 11G5, and 10D8 antibodies bound the peptide spanning residues approximately 301–324, and thus span the clip site. Monoclonal antibodies other than 10F6, 11G5, and 10D8 which are capable of doing so are useful in the practice of this invention, despite any differences in affinity, immunoglobulin class, species of origin, or gp120 epitope, as are antibodies which are expressed in recombinant cell culture or that are predetermined amino acid sequence variants of the 10F6, 11G5, and 10D8 antibodies, e.g. chimeras of the variable region of the 10F6, 11G5, and 10D8 antibodies and a human constant region.

The route and schedule of immunization of the host animal or cultured antibody-producing cells therefrom are generally in keeping with established and conventional techniques for antibody stimulation and production. Applicants have employed mice as the test model although it is contemplated that any mammalian subject including human subjects or antibody producing cells therefrom can be manipulated according to the processes of this invention to serve as the basis for production of mammalian, including human, hybrid cell lines.

After immunization, immune lymphoid cells are fused with myeloma cells to generate a hybrid cell line which can be cultivated and subcultivated indefinitely, to produce large quantities of monoclonal antibodies. For purposes of this invention, the immune lymphoid cells selected for fusion are lymphocytes and their normal differentiated progeny, taken either from lymph node tissue or spleen tissue from immunized animals. Applicants prefer to employ immune spleen cells, since they offer a more concentrated and convenient source of antibody producing cells with respect to the mouse system. The myeloma cells provide the basis for continuous propagation of the fused hybrid. Myeloma cells are tumor cells derived from plasma cells.

It is possible to fuse cells of one species with another. However, it is preferred that the source of immunized antibody producing cells and myeloma be from the same species.

The hybrid cell lines can be maintained in culture in vitro in cell culture media. The cell lines of this invention can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, Ion exchange chromatography, affinity chromatography, or the like. The antibodies described herein are also recovered from hybridoma cell cultures by conventional methods for purification of IgG or IgM as the case may be that heretofore have been used to purify these immunoglobulins from pooled plasma, e.g. ethanol or polyethylene glycol precipitation procedures. The purified antibodies are sterile filtered, and optionally are conjugated to a detectable marker such as an enzyme or spin label for use in diagnostic assays of HIV in test samples.

While the invention is demonstrated using mouse monoclonal antibodies, the invention is not so limited; in fact, human antibodies may be used and may prove to be preferable. Such antibodies can be obtained by using human hybridomas (Cote et al., *Monoclonal Antibodies and Cancer Therapy,* Alan R. Liss, p. 77 (1985)). In fact, according to the invention, techniques developed for the production of chimeric antibodies (Morrison et al., *Proc. Natl. Acad. Sci.,* 81:6851 (1984); Neuberger et al., *Nature* 312:604 (1984); Takeda et al., *Nature* 314:452 (1985)) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention.

As another alternative to the cell fusion technique, EBV-immortalized B cells are used to produce the monoclonal antibodies of the subject Invention. Other methods for producing monoclonal antibodies such as recombinant DNA, are also contemplated.

Immunotoxins

This invention is also directed to immunochemical derivatives of the antibodies of this invention such as immunotoxins (conjugates of the antibody and a cytotoxic moiety). The antibodies are also used to induce lysis through the natural complement process, and to interact with antibody dependent cytotoxic cells normally present.

Purified, sterile filtered antibodies are optionally conjugated to a cytotoxin such as ricin for use in AIDS therapy. U.S. patent application Ser. No. 07/350,895 illustrates methods for making and using immunotoxins for the treatment of HIY infection, and its teachings are specifically incorporated by reference herein.

Immunotoxins of this invention, capable of specifically binding HIV env, are used to kill cells that are already infected and are actively producing new virus. Killing is accomplished by the binding of the immunotoxin to viral coat protein which is expressed on infected cells. The immunotoxin is then internalized and kills the cell. Infected cells that have incorporated viral genome into their DNA but are not synthesizing viral protein (i.e., cells in which the virus is latent) may not be susceptible to killing by immunotoxin until they begin to synthesize virus. The antibodies of this invention which span the clip site and/or the other antibodies described herein may be used alone or in any combination with for delivering toxins to infected cells. In addition, a toxin-antibody conjugate can bind to circulating viruses or viral coat protein which will then effect killing of cells that internalize virus or coat protein. The subject invention provides a highly selective method of destroying HIV infected cells, utilizing the antibodies described herein.

While not wishing to be constrained to any particular theory of operation of the invention, it is believed that the expression of the target antigen on the infected cell surface is transient. The antibodies must be capable of reaching the site on the cell surface where the antigen resides and interacting with it. After the antibody complexes with the antigen, endocytosis takes place carrying the toxin into the cell.

The immunotoxins of this invention are particularly helpful in killing monocytes/macrophages infected with the HIV virus. In contrast to the transient production of virus from T cells, macrophages produce high levels of virus for long periods of time. Current therapy is ineffective in inhibiting the production of new viruses in these cells.

Not all monoclonal antibodies specific for HIV env or unclipped HIV env make highly cytotoxic immunotoxins, however assays are routinely and commonly used in the field to predict the ability of an antibody to function as part of a immunotoxin. Preferably the antibodies used cross react with several (or all) strains of HIV.

The cytotoxic moiety of the immunotoxin may be a cytotoxic drug or an enzymatically active toxin of bacterial, fungal, plant or animal origin, or an enzymatically active fragment of such a toxin. Enzymatically active toxins and fragments thereof used are diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. In another embodiment, the antibodies are conjugated to small molecule anticancer drugs such as cis-platin or 5FU. Conjugates of the monoclonal antibody and such cytotoxic moieties are made using a variety of bifunctional protein coupling agents. Examples of such reagents are SPDP, IT, bifunctional derivatives of imidoesters such as dimethyl adipimidate HCI, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)--ethylenediamine, diisocyanates such as tolylene 2,6-diisocyanate and bis-active fluorine compounds such as 1,5-difluoro-2,4-dinitrobenzene. The lysing portion of a toxin may be joined to the Fab fragment of the antibodies.

Immunotoxins can be made in a variety of ways, as discussed herein. Commonly known crosslinking reagents can be used to yield stable conjugates.

Advantageously, monoclonal antibodies specifically binding the domain of the protein which is exposed on the infected cell surface, are conjugated to ricin A chain. Most advantageously the ricin A chain is deglycosylated and produced through recombinant means. An advantageous method of making the ricin immunotoxin is described in Vitetta et al., *Science* 238:1098 (1987) hereby incorporated by reference.

When used to kill infected human cells in vitro for diagnostic purposes, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques.

Cytotoxic radiopharmaceuticals for treating infected cells may be made by conjugating radioactive isotopes (e.g. I, Y, Pr) to the antibodies. Advantageously alpha particle-emitting isotopes are used. The term "cytotoxic moiety" as used herein is intended to include such isotopes.

In a preferred embodiment, ricin A chain is deglycosylated or produced without oligosaccharides, to decrease its clearance by irrelevant clearance mechanisms (e.g., the liver). In another embodiment, whole ricin (A chain plus B chain) is conjugated to antibody if the galactose binding property of B-chain can be blocked ("blocked ricin").

In a further embodiment toxin-conjugates are made with Fab or F(ab')$_2$ fragments. Because of their relatively small size these fragments can better penetrate tissue to reach infected cells.

In another embodiment, fusogenic liposomes are filled with a cytotoxic drug and the liposomes are coated with antibodies specifically binding HIV env.

Antibody Dependent Cellular Cytotoxicity

The present invention also involves a method based on the use of antibodies which are (a) directed against HIV env or unclipped HIV env, and (b) belong to a subclass or isotype that is capable of mediating the lysis of HIV virus infected cells to which the antibody molecule binds. More specifically, these antibodies should belong to a subclass or isotype that, upon complexing with cell surface proteins, activates serum complement and/or mediates antibody dependent cellular cytotoxicity (ADCC) by activating effector cells such as natural killer cells or macrophages.

The present invention is also directed to the use of these antibodies, in their native form, for AIDS therapy. For example, IgG2a and IgG3 mouse antibodies which bind HIV-associated cell surface antigens can be used in vitro for AIDS therapy. In fact, since HIV env is present on infected monocytes and T-lymphocytes, the antibodies disclosed herein and their therapeutic use have general applicability.

Biological activity of antibodies is known to be determined, to a large extent, by the Fc region of the antibody molecule (Uananue and Benacerraf, *Textbook of Immunology*, 2nd Edition, Williams & Wilkins, p. 218 (1984)). This includes their ability to activate complement and to mediate antibody-dependent cellular cytotoxicity (ADCC) as effected by leukocytes. Antibodies of different classes and subclasses differ in this respect, and, according to the present invention, antibodies of those classes having the desired biological activity are selected. For example, mouse immunoglobulins of the IgG3 and IgG2a class are capable of activating serum complement upon binding to the target cells which express the cognate antigen.

In general, antibodies of the IgG2a and IgG3 subclass and occasionally IgG1 can mediate ADCC, and antibodies of the IgG3, IgG2a, and IgM subclasses bind and activate serum complement. Complement activation generally requires the binding of at least two IgG molecules in close proximity on the target cell. However, the binding of only one IgM molecule activates serum complement.

The ability of any particular antibody to mediate lysis of the target cell by complement activation and/or ADCC can be assayed. The cells of interest are grown and labeled in vitro; the antibody is added to the cell culture in combination with either serum complement or immune cells which may be activated by the antigen antibody complexes. Cytolysis of the target cells is detected by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

Antibodies of virtually any origin can be used for this purpose provided they bind a HIV env epitope and can activate complement or mediate ADCC. Monoclonal antibodies offer the advantage of a continuous, ample supply. In fact, by immunizing mice with gp160 establishing hybridomas making antibodies to HIV env and selecting hybridomas making antibodies which can lyse infected cells in the presence of human complement, it is possible to rapidly establish a panel of antibodies capable of reacting with and lysing infected cells.

Therapeutic and Other Uses of the Antibodies

When used in vivo for therapy, the antibodies of the subject invention are administered to the patient in therapeutically effective amounts (i.e. amounts that restore T cell counts). They will normally be administered parenterally. The dose and dosage regimen will depend upon the degree of the infection, the characteristics of the particular immunotoxin (when used), e.g., its therapeutic index, the patient, and the patient's history. Advantageously the immunotoxin is administered continuously over a period of 1–2 weeks, intravenously to treat cells in the vasculature and subcutaneously and intraperitoneally to treat regional lymph nodes. Optionally, the administration is made during the course of adjunct therapy such as combined cycles of tumor necrosis factor and interferon or other immunomodulatory agent.

For parenteral administration the antibodies will be formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate can also be used. Liposomes may be used as carriers. The vehicle may contain minor amounts of additives such as substances that enhance isotonicity and chemical stability, e.g., buffers and preservatives. The antibodies will typically be formulated in such vehicles at concentrations of about 1 mg/ml to 10 mg/ml.

Use of IgM antibodies is not currently preferred, since the antigen is highly specific for the target cells and rarely occurs on normal cells. IgG molecules by being smaller may be more able than IgM molecules to localize to infected cells.

There is evidence that complement activation in vivo leads to a variety of biological effects, including the induction of an inflammatory response and the activation of macrophages (Uananue and Benecerraf, *Textbook of Immunology*, 2nd Edition, Williams & Wilkins, p. 218 (1984)). The increased vasodilation accompanying inflammation may increase the ability of various anti-AIDS agents to localize in infected cells. Therefore, antigen-antibody combinations of the type specified by this invention can be used therapeutically in many ways. Additionally, purified antigens (Hakomori, *Ann. Rev. Immunol.* 2:103 (1984)) or anti-idiotypic antibodies (Nepom et al., *Proc. Natl. Acad. Sci.* 81:2864 (1985); Koprowski et al., *Proc. Natl. Acad. Sci.* 81:216 (1984)) relating to such antigens could be used to induce an active immune response in human patients. Such a response includes the formation of antibodies capable of activating human complement and mediating ADCC and by such mechanisms cause infected cell destruction.

The antibodies of the subject invention are also useful in the diagnosis of HIV in test samples. They are employed as one axis of a sandwich assay for HIV env or unclipped HIV env, together with a polyclonal or monoclonal antibody directed at another sterically-free epitope of HIV env of unclipped HIV env. For use in some embodiments of sandwich assays the 10F6, 11G5, or 10D8 antibody or its equivalent is bound to an insolubilizing support or is labelled with a detectable moiety following conventional procedures used with other monoclonal antibodies. In another embodiment a labelled antibody, e.g. labelled goat anti-murine IgG, capable of binding the 10F6, 11G5, or 10D8 antibody is employed to detect HIV env or unclipped HIV env binding using procedures previously known per se.

The antibodies of this invention which are directed to an epitope spanning the clip site are used for producing unclipped HIV env. This method comprises the following general steps: First, contacting a first preparation of HIV env with an antibody directed to an HIV env epitope spanning the clip site for a time sufficient to permit formation of a second, antibody-bound HIV env, preparation; secondly, separating the second preparation from any HIY env which is not antibody-bound; and thirdly recovering the unclipped HIV env from said second preparation. These methods are used with standard procedures for affinity purification and affinity chromatography, and may use antibody which is immobilized on a water insoluble support as discussed above. Any known procedure for immobilizing monoclonal antibodies can be used for this purpose.

The antibody compositions used in therapy are formulated and dosages established in a fashion consistent with good medical practice taking into account the disorder to be treated, the condition of the individual patient, the site of delivery of the composition, the method of administration and other factors known to practitioners. The antibody compositions are prepared for administration according to the description of preparation of polypeptides for administration, infra.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

In particular, it is preferred that these plasmids have some or all of the following characteristics: (1) possess a minimal number of host-organism sequences; (2) be stable in the desired host; (3) be capable of being present in a high copy number in the desired host; (4) possess a regulatable promoter; and (5) have at least one DNA sequence coding for a selectable trait present on a portion of the plasmid separate from that where the novel DNA sequence will be inserted. Alteration of plasmids to meet the above criteria are easily performed by those of ordinary skill in the art in light of the available literature and the teachings herein. It is to be understood that additional cloning vectors may now exist or will be discovered which have the above-identified properties and are therefore suitable for use in the present invention and these vectors are also contemplated as being within the scope of this invention.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.* 8: 4057 (1980).

"PCR" (polymerase chain reaction) refers to a technique whereby a piece of DNA is amplified. Oligonucleotide primers which correspond to the 3' and 5' ends (sense or antisense strand-check) of the segment of the DNA to be amplified are hybridized under appropriate conditions and the enzyme Taq polymerase, or equivalent enzyme, is used to synthesize copies of the DNA located between the primers.

"Dephosphorylation" refers to the removal of the terminal 5 ' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional. Maniatis, T. et al., *Molecular Cloning pp.* 133–134 (1982). Reactions using BAP are carried out in 50 mM Tris at 68° C. to suppress the activity of any exonucleases which are present in the enzyme preparations. Reactions are run for 1 hour. Following the reaction the DNA fragment is gel purified.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T. et al., Id., p. 146). Unless otherwise provided, ligation is accomplished using known buffers and conditions with 10 units of T4 DNA ligase ("ligase") per 0.5 μg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 μg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase I and 250 μM of each of the four deoxynucleoside triphosphates. The incubation generally is terminated after 30 min. phenol and chloroform extraction and ethanol precipitation.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention. All literature citations herein are expressly incorporated by reference.

Deposit of Materials

The following cultures have been deposited with the American Type Culture Collection, 12301 Parklawn Drive, Rockville, Md., USA (ATCC):

| Strain | ATCC Dep. No. | Deposit Date |
| --- | --- | --- |
| gp120 in | — | — |
| 6E10 | CRL 10514 | 26 JULY 1990 |
| 5B3 | CRL 10515 | 26 JULY 1990 |
| 13H8 | CRL 10510 | 26 JULY 1990 |
| 10F6 | CRL 10512 | 26 JULY 1990 |
| 11G5 | CRL 10511 | 26 JULY 1990 |
| 6D8 | — | — |
| 10D8 | CRL 10513 | 26 JULY 1990 |

These deposits were made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.12 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiments are intended to illustrate only certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

EXAMPLES

Example 1. Chimpanzee Vaccine Study

Previous literature reported that chimpanzees immunized with recombinant gp120 (rgp120) developed humoral and cellular immunity to virus-derived protein, but that vaccination with this preparation failed to provide protection from HIV-1 infection in vivo (e.g. Berman et al., *Proc.Nat.Acad. .Sci.USA* 85: 5200–5204, 1988 and other references, infra. Surprisingly, our present study demonstrates a vaccine which did provide protection.

The proteins used in this study were purified preparations of recombinant protein expressed in mammalian cell culture and adsorbed onto aluminum gel.

Figure 3A:
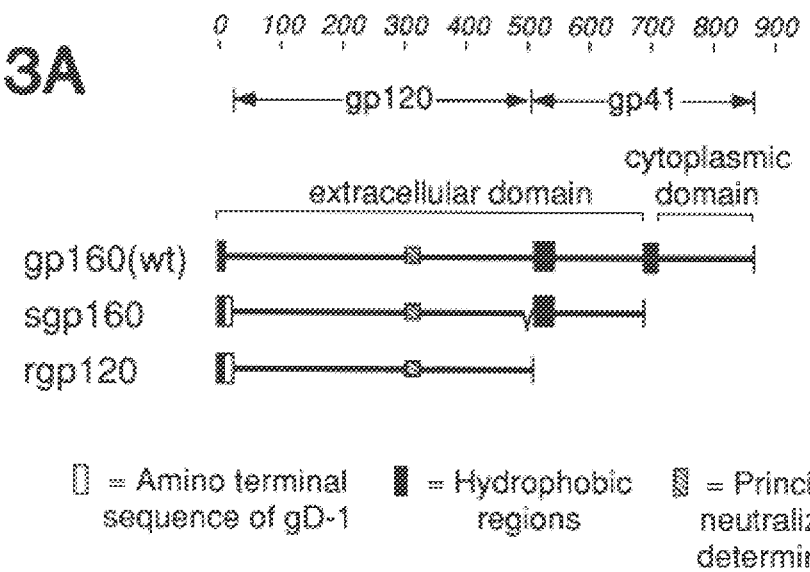

The rgp120 protein (FIG. 3A) consists of the gp120 fragment of the HIV-1 envelope glycoprotein fused to a short N-terminal sequence of the herpes simplex virus glycoprotein D to facilitate expression. The sgp160 protein is a variant of gp160 wherein the transmembrane domain and cytoplasmic tail have been deleted to enable the protein to be secreted from mammalian cells. Both proteins are glycosylated in a manner similar to authentic viral gp120, and bind to CD4, the cellular receptor for HIV-1, with high affinity.

The immunogens used in this study, rgp120 and sgp160, were purified by immunoaffinity chromatography using different monoclonal antibodies for each antigen, as described above. Besides the absence of contaminating proteins, a major difference between the gp120 used in this study and previous studies is that the present study used gp120 which was not proteolyzed. Evaluation of material used in previous studies shows that approximately 50% of the gp120 in recombinant preparations was proteolytically clipped at amino acid 315 to yield peptides that migrated on SDS PAGE gels with mobilities of 50 kd and 75 kd. We have determined that this proteolysis site is located in the middle of a major type-specific neutralizing epitope (shown as IV on FIG. 1). In this study, we used unclipped gp120, but the sgp160 preparation used exhibited approximately 50% proteolysis at this position.

In the present study, two chimpanzees were immunized with the 140–150 kd sgp160 protein, and two chimpanzees were immunized with the 120–130 kD rgp120 protein. A placebo control animal was immunized with the same quantity of recombinant glycoprotein D (gD-1) of herpes simplex virus type 1, expressed in mammalian cell culture, purified by a similar procedure as the rgp 120 (Berman et al., *Science* 277:1490–1492 (1985)), and adsorbed onto aluminum gel. Specifically, animals were immunized with I ml of a preparation of antigen at a dose of 300 µg of protein per animal per immunization.

All antigens were formulated in an aluminum hydroxide (alum) adjuvant (Berman et al., *Proc. Natl. Acad. Sci. USA* 85:5200–5204 (1988) (0.5 mg/ml of $Al^{+3}$) in phosphate buffered saline (0.016M $PO_4$ pH 6.2, 0.15M NaCl, 0.004M KCl), the only adjuvant currently approved in the United States for vaccine products.

The immunization schedule that we employed was different from all published HIV or SIV vaccine trials, but was similar to that used for the Hepatitis B virus vaccine which was found to give good results in dose interval studies in other primates (Anderson et al., *J. Infect. Diseases* 160:960–969 (1989). Animals were given a primary immunization with either unclipped rgp120 or sgp160 at time 0, followed by booster immunizations at four weeks and thirty-two weeks. Test and control preparations were administered intramuscularly in two sites (0.5 ml/site).

Blood samples were taken from each animal at bimonthly intervals and analyzed by a number of assays. Besides immunological assays (e.g. antibody titers to gp120, lymphocytes proliferation assays), the level of T cell subsets, serum enzyme levels, and clinical chemistries were monitored. As reported previously, we found no abnormalities in lymphocyte subsets, lymphocyte function, serum enzyme levels, or blood chemistries resulting from immunization with these proteins. Thus concerns that immunization with rgp120 or sgp160 might lead to untoward side effects ( e.g. immunosuppression or autoimmunity) could not be validated by these studies.

After the primary immunization, a low level of antibodies to sgp160 but not rgp120 were detected by commercial (Dupont or Biorad) HIV-1 immunoblot assays, but not (FIG. 6A) in a liquid-phase radioimmunoprecipitation assay (RIA) or a commercial (Genetic Systems) HIV-1 antibody test (ELISA). A second immunization at four weeks elicited a moderate humoral and cellular immune response to both of the HIV-1 derived immunogens that could be detected in a liquid phase radioimmunoprecipitation assay (RIP) (FIG. 6A) and immunoblot assays (data not shown), but not by ELISA. The third immunization, given at 32 weeks (seven months following the second) resulted in a marked increase in antibody titers apparent in all three antibody assays (FIGS. 6 and 7). Immunoblot analysis (FIG. 7) of the serum collected three weeks after the last boost (week 35) showed that those that received rgp120 reacted strongly with HIV-1 gp120 and to a lesser extent with gp160. Animals immunized with rgp160 reacted, as intended, with viral gp16, and gp41 as well as gp120. Also evident in immunoblots were antibodies reactive with proteolytic breakdown products of gp120. Cellular immunity, as indicated by the ability of rgp120 to stimulate lymphocyte proliferation, could be detected at this time in the rgp120 and sgp160 immunized animals but not in the control (Table 2).

The increase in antibody titers to rgp120 and sgp160 observed after the third immunization was coincident with the appearance of neutralizing antibodies (Robertson, et al., J. Virol. Methods. 20:195–202 (1988)) (FIG. 8A). The time required to attain the peak neutralizing titer varied from two to four weeks after boosting, however no significant difference in the magnitude of the peak in vitro neutralizing titers was detected between those animals immunized with rgp120 and with sgp160. One animal from each group exhibited peak neutralizing titers of 1:640 whereas the remaining animals in each group possessed peak titers of 1:320. Significantly, these neutralizing responses were far greater than those observed previously (Berman et al., 1988, supra) where the neutralizing activity of sera to rgp120 could only be detected at a 1:5 dilution in a neutralizing assay with comparable sensitivity. Thus, the immunogens and immunization procedures used in the present study elicited a neutralizing response that was 1–2 orders of magnitude greater than that previously observed.

Based on the significant levels of neutralizing antibodies, we proceeded with a virus challenge of these animals. All five animals were intravenously injected, three weeks after the final immunization (week 35), with approximately 40 tissue culture infectious dose units ($TCID_{50}$) of virus derived from a standard inoculum of the IIIB isolate of HIV-1 (kindly provided by Dr. L. Arthur, National Cancer Institute, National Institute of Health, Bethesda Md., USA) that has been used for many other chimpanzee infectivity studies (Arthur et al., supra, and Prince et al., supra). The envelope protein from this isolate is 98% identical in amino acid sequence with that used to produce the rgp120 and sgp160 immunogens, described above. The amount of virus was used in this study was the same for all challenged animals and corresponded to approximately ten chimpanzee infectious doses ($CID_{50}$) Blood was taken from the animals at bimonthly interval and was subjected to a battery of assays to detect viral infection.

After virus challenge, the magnitude and the duration of the anti-rgp120 antibody response in the rgp120 immunized animals differed markedly from the other animals in teh study. The titer of anti-gp120 antibodies in these animals as measured by RIA did not increase after virus challenge, but rather, progressively declined to baseline values (Table 2). In contrast, the titer of anti-gp120 antibodies in the animals immunized with sgp160 modestly declined for approximately 7–8 weeks after virus challenge, then increased to a titer somewhat higher than the peak achieved by hyperimmunization, and then leveled off at an intermediate titer. These results suggested that HIV-1 challenge of teh sgp160 immunized animals resulted in viral infection and the production of sufficient viral protein to stimulate an anamnestic immune response. The observation that the titer of antibodies to gp120 in the rgp120 -immunized animals did not increase after challenge, but in fact disappeared with time, suggests that a productive infection did not occur. Antibodies reactive with rgp 120 were detected in the control animal by RIA at 16 weeks post challenge, indicating that this animal also became infected with HIV-1.

Analysis of these sera by ELISA using commercially available HIV-1 antibody assay (FIG. 6B) showed a pattern of activity that differed form that detected in the anti-gp120 RIA. In this assay, antibodies to HIV-1 were detected only after the third immunization, and the antibody response present was significantly greater in the rgp160-immunized animals than in the rgp120 animals. This difference reflects the fact that the commercial HIV-1 antibody assays typically possess less gp120 than gp41. Sera from the sgp160-immunized animals gave a strong reaction in this assay because they contained antibodies to gp41 as well as gp 120. The control animal showed no signs of HIV-1 reactive antibodies at any time prior to HIV-1 challenge. The HIV-1 antibody titers in the animals immunized with rgp160 declines for approximately 6–7 weeks after virus challenge, and then increased to a level similar to that obtained by hyperimmunization and then declined to intermediate values. In contrast, ELISA titers in teh rgp 120-immunized animals did not increase, but rather progressively declined to baseline values by 7 weeks post challenge (Table 2, FIG. 6B). This result further demonstrated that there was not sufficient replication of HIV-1 in the rgp120-immunized animals to elicit an immune response to any of the viral antigens contained in the HIV-1 antibody assay. The control animal was negative in this assay at the time of challenge, but became positive in response to viral infection at 13 weeks post challenge, indicating that this animal became infected with HIV-1.

Immunoblot analysis of chimpanzee sera showed that at the time of challenge the sera from the rgp120 and sgp160-immunized animals possessed antibodies to the HIV-1 envelope glycoproteins, but not to the core proteins (e.g. p17, p24, and p55). Serologic evidence of HIV-1 infection in the two sgp160-immunized animals was first noted at 5 weeks post challenge where a faint p24 band appeared (data not shown). Antibodies to p17 and p55 became apparent at later dates (Table 2, FIG. 7). Antibodies to p24 were first detected in the sera of the control animal at 9 weeks post challenge (data not shown), and reactivity with p17, p55 and gp120 could be detected at later dates. Interestingly, the intensity of the antibody response to HIV-1 structural proteins (e.g. p55, p24 and p17) was far greater in the sgp160-immunized animals (FIG. 7) than in the control. Antibodies to gp120 were present in the rgp120-immunized animals at the time of challenge, but had largely disappeared by 13 weeks post challenge (FIG. 7). Significantly, the animals immunized with rgp120 have not, as of 26 weeks post challenge, seroconverted to any of the HIV-1 encoded proteins other than gp120, suggesting that they were resistant to HIY-1 infection.

Changes in the concentration of neutralizing antibodies after HIV-1 challenge paralleled those seen in the anti-gp120 titers (FIGS. 6A and 7). Thus, the 32-week immunization elicited a high level of neutralizing antibodies in the rgp 120 and sgp160-immunized animals which persisted through the time of HIV-1 challenge at 35 weeks (Table 2). The neutralizing titers in the rgp120-immuniZed animals reached peak titers by the time of virus challenge and the n steadily wanted to the level of pre-immune sera by 60 weeks. The neutralizing titers in both of the sgp160-immunized animals declined for several weeks but sharply increased at 7 weeks post-challenge, presumably in response to the production of viral proteins. Neutralizing titers in one of the sgp 160 animals rose to values of 1:1280 by 13 weeks post challenge. Neutralizing antibodies were not detected in the control until 17 weeks post challenge. The results of these assays provided further evidence that HIV-1 did not replicate in the rgp120-immunized animals but did so in the control and the sgp160-immunized animals.

Virus co-cultivation studies were carried out in order to determine whether viable virus could be recovered from any of the immunized animals. HIV-1 could be recovered from the control and the sgp160-immunized animals at 6–7 weeks post challenge (Table 2) but has never been recovered from either of the rgp120-immunized animals at any time up to 6 months post challenge. Further evidence of HIV-1 infection in the control and the two sgp160-immunized animals was provided by PCR analysis (Table 2) where proviral DNA could be detected in these animals, but not the rgp120-immunized animals. Taken together, these results suggest that immunization with rgp 120 elicited a protective immune response which has significantly delayed or completely prevented infection of these animals by HIV-1.

Since the levels of neutralizing antibodies present in the rgp120 and sgp160-immunized chimps were essentially identical over the four-week interval that followed the last boost, it was surprising that only the rgp120-immunized animals were protected from HIV-1 infection. One explanation for the difference in susceptibility to HIV-1 infection between the two groups of animals is that on the actual day of virus challenge, the sgp160—immunized animals had slightly lower neutralization titers (i.e. 1:160) than the rgp120-immunized animals which exhibited neutralization titers of 1:320 and 1:640. If the level of antibody present on the actual day of challenge is of overriding importance, than our data suggest that titers of >1:160 are required to prevent infection. On balance, we considered it unlikely that there is such a discrete threshold in protection from infection and postulated that other factors may be involved.

Additional studies were carried out to determine whether antibodies to specific epitopes of functional significance might better correlate with protection. We reasoned that antibodies able to block the binding of gp120 to CD4 might play an important role. Previously, (Berman et al., *J. Virol.* 63:3489–3498 (1989); Lasky et al., *Cell* 50:975–985 (1987)) we noted that rgp120 and sgp160 were both effective in eliciting antibodies that disrupted this interaction. Analysis of sera at the time of challenge showed that all the animals with the HIV-1 derived immunogens possessed antibodies that blocked CD4 binding, and that the blocking titer did not correlate with protection from infection or with neutralizing titer (Table 2). Another possibility we considered was whether a subpopulation of neutralizing antibodies might account for the difference in protection between the rgp120 and wgp160 treated animals. In these studies we assayed the sera for antibodies reactive with a peptide within the V3 domain of gp120 known to contain the major type-specific neutralizing determinant (MND) (Matsushita et al., *J. Virol.* 62:2104–2114 (1988)).

Antibodies to this epitope were detected using an ELISA assay incorporating a synthetic MND peptide, RP135, described by Matsushita, ibid. When sera form the rgp120 and sgp160-immunized animals were compared, we found that antibody binding to the MND peptide differed significantly between the two groups of animals (Table 2, FIG. 8B). At the time of challenge, there was almost a ten-fold difference in the amount of antibodies to the MND in the animals immunized with rgp120 compared to those immunized with sgp160. Especially interesting was the observation that one animal, which had the lowest anti-gp120 titer by RIA, had the highest titer to the MND, and was protected from infection. Thus, the correlation between protection and the level of antibodies to the MND appeared to be stronger than the correlation between protection and the level of antibodies to the MND appeared to be stronger than the correlation between neutralizing antibodies and protection.

The difference in the formation of antibodies to the MND may be attributable to the difference the amount of proteolytic processing (FIG. 3) between the two preparations (ie. 40% for sgp160 and 5% for rgp120 ) especially since the clip site, in this instance arginine residue 312, is located within a disulfide bonded loop that contains the MND. It should be noted that proteolysis at this position does not appear to cause a major conformational change in either rgp120 or sgp160 since proteolyzed material is able to bind to CD4 with high affinity (Berman and Gregory, unpublished results). As with the RIA titers and the HIV-1 antibody titers, we found that the concentration of antibodies to this epitope reached maximum values in the rgp120 animals shortly after the final immunization (32 weeks) and then progressively declined to baseline values. Antibodies from the sgp160 immunized animals peaked shortly after the last injection and proceeded to decline for several weeks, then increased and have remained positive at more than 25 weeks post challenge. Antibodies to the MND appeared in the control animal at 15 weeks post challenge.

Another significant result of these studies is that there are at least two populations of antibodies able to neutralize HIV-1 infectivity in vitro. One population is elicited to rgp120 and is presumably directed towards the MND. A second population is elicited by immunization with rsgp160 and is directed towards sites other than the MND. While the hypothesis that in vivo protection is dependent on the presence of antibodies to the MND is supported by the data for the rgp 120 immunized animals, we cannot be certain that the lack of protection in the sgp160 immunized animals was due to a low level of antibodies to the MND. An alternative explanation, that would also fit our data, is that the neutralizing antibodies elicited by sgp160 to sites other than the MND are, in fact, able to provide protection in vivo, but that some factor interferes with or abrogates their protective effect. There have been several reports of antibodies to HIV-1 that enhance rather than inhibit viral infection in vitro (Homsy et al., *Science* 244:1357–1359 (1989); Robinson et al., *Lancet* 1:790–794 (1988). An enhancing epitope contained on sgp160, but not rgp120 might account for the difference in protection that we have observed. This possibility would be consistent with the observation that the animals immunized with sgp160 (x-247 and x-261) seroconverted to HIV-1 core proteins earlier (5 weeks post challenge) than the control (x-246) which seroconverted at 11 weeks post challenge (Table 2), and that the intensity of the immune response, as visualized in the immunoblot assay, was much greater for these animal that for the control (FIG. 7). Recently, two different enhancing epitopes have been mapped to a region of gp41 (Robinson et al., *Proc. Natl. Acad. Sci. USA* (in press))that was present on the sgp160 immunogen, but not the rgp120 immunogen.

Figure 3B:
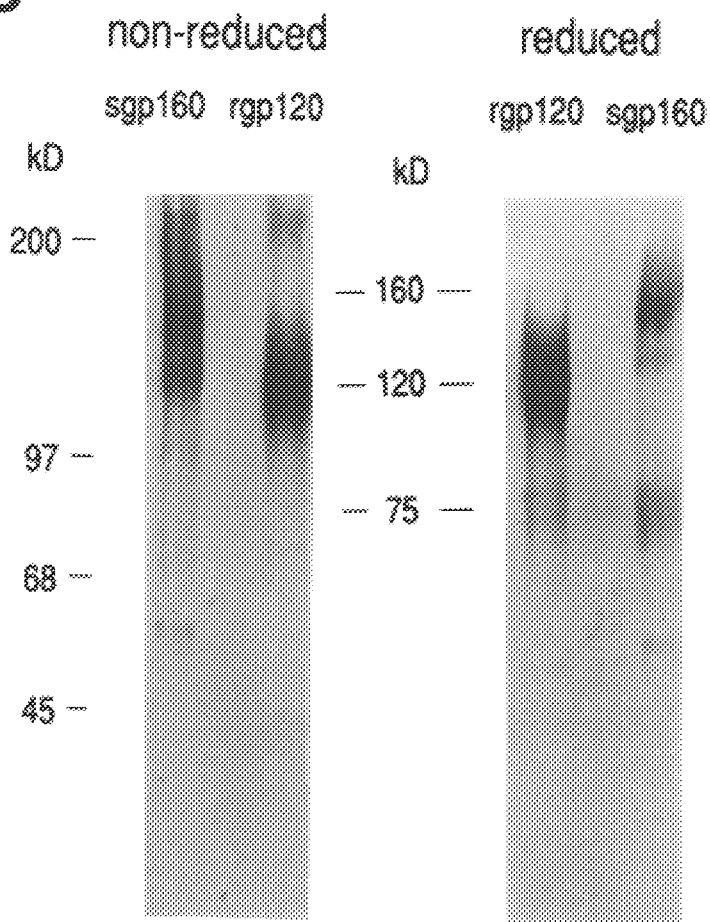

Several factors may account for the success of rgp120 in the current study as compared to our previous study (Berman et al., supra) where rgp120 failed to provide protection from HIV-1 infection. One significant difference was that the animals were immunized according to an optimized immunization protocol, whereas previously an immunization protocol that had been adapted from rodent studies was employed. Another important difference was that the rgp120 used in the earlier study was only 50% pure and was approximately 50% clipped, whereas the rgp120 employed in the present studies was <5% clipped (FIG. 3). A third difference was that in the previous study the animals were challenged with 100 $TCID_{50}$ units (25 $CID_{50}$) of HIV-1, whereas in the present study the animals were challenged with 40 TCID50 units of virus (10 $CID_{50}$). A final explanation for the difference between the present study and the previous study relates to the experimental design. Because the availability of chimpanzees restricts the size of the treatment groups to only a few animals, the ability to show statistical significance in chimpanzee efficacy studies is limited. Thus, negative results are uninterpretable and do not allow us to discern whether the rgp120 used in the previous studies, or the sgp160 employed in the present study, did or did not confer some significant level of protective immunity.

This application represents the first report, to our knowledge, of a candidate AIDS vaccine that has succeeded in protecting chimpanzees from HIV-1 infection. Significantly, the recombinant subunit vaccine described herein consists of a single purified protein, prepared entirely from non-infectious materials, and is effective in an adjuvant approved for human use.

TABLE 2

Immunologic and Virologic Characteristic Of Chimpanzees Before and After HIV-1 Infection*

I. Characteristics at the time of virus challenge (35 weeks)

|  | CONTROL | SGP160 |  | RGP120 |  |
| --- | --- | --- | --- | --- | --- |
|  | x246 | x247 | x261 | x262 | x265 |
| 1. Anti-gp120 Titer | – | 4.3 | 4.3 | 4.8 | 3.9 |
| 2. Antibodies to gp41 | – | + | + | – | – |
| 3. HIV-1 ELISA Titer | <2400 | 6400 | 25,600 | 3200 | 400 |
| 4. Proliferation to rgp120 | — | + | + | + | + |
| 5. Neutralizing Titer | <10 | 160 | 160 | 320 | 640 |
| 6. CD4 Blocking Antibodies | <1 | 2.2 | 2.5 | 2.5 | 1.7 |
| 7. Anti-MND Titer | <10 | 145 | 149 | 491 | 844 |
| II. Characteristics After HIV-1 Challenge |  |  |  |  |  |
| 1. 1ST Cocultivation of HIV-1 | 6 | 6 | 7 | – | – |
| 2. Time to anti-p24 (wk) | 11 | 5 | 5 | – | – |
| 3. Time to p17 (wk) | 13 | 5 | 5 | – | – |
| 4. PCR (53 wk) | + | + | + | – | – |
| 5. HIV-1 ELISA Titer (60 wk) | 800 | 3200 | 6400 | <400 | <400 |
| 6. Neutralizing Titer (60 wk) | 10 | 80 | 80 | <10 | <10 |
| 7. Proliferation to rgp120 (60 wk) | – | + | + | – | – |
| 8. Anti-gp120 Titer (63 wk) | – | 3.2 | 2.9 | – | – |

* Legend To Table 2: Antibody titers to gp120 were determined in a liquid phase RIA; the data presented represent log values from endpoint dilution titrations (see description of FIG. 6A). The presence of antibodies to gp41 and the time to appearance of antibodies to p24 and p17 were determined by immunoblot analysis of sequential bleeds using commercial (Dupont and Biorad) Western blot strips. Antibodies that block the binding of gp120 to CD4 were measured as described previously; data represents the log of endpoint dilution titrations. HIV-1 ELISA titers were determined in a commercial HIV-1 antibody assay kit (see description of FIG. 6B). The cocultivation of HIV-1 and the proliferation of chimpanzee lymphocytes to rgp120 was carried out as described previously. In vitro neutralizing antibodies were measured by the method of Robertson, et al.. supra. (see description to FIG. 8). Anti-MND titers were determined in an ELISA assay as described above. PCR reactivity determined using the method of Kellog and Kwok, in PCR Protocols (Innis et al., eds) 337–347 (Academic Press, New York, 1990). Briefly, frozen lymphocytes were processed in PCR lysis buffer and the DNA was phenol-chloroform extracted and ethanol precipitated. A sample of the DNA (equivalent to the amount in 150,000–300,000 cells) was subjected to 40 cycles of PCR using the SK68 and SK69 primers. Samples were adjusted to 25 mM NaCl and hybridized in solution for 30 min at 55° C. to 0.5 pmol of primer SK70 end labeled with gamma labeled [$^{32}$P]— ATP. Samples were resolved on a 10% acrylamide minigel in TBE buffer. The gel was then dried and used to expose an x-ray film. Positive control DNA was prepared from a transfected CHO cell line expressing gp160. DNA samples were tested for their ability to be amplified using probes to beta globin. Sample were considered positive for HIV-1 if the labeled primer hybridized to a band of 141 base pairs.

Example 2. Generation of Antibodies

1. Generation and Characterization of Monoclonal Antibodies.

Soluble forms of recombinant gp120 and gp160 were expressed in Chinese Hamster Ovary (CHO) cells according to the methods described in Lasky et al., Science 223: 209 (1986), and were purified by affinity chromatography from growth conditioned cell culture medium of the D531 and D683.DC.9 cell lines described previously. The soluble form of recombinant gp 160 (sgpl60 or 683DC.7) contained two deletions. The first eliminated ten amino acids spanning the gp120/41 cleavage site and the second deleted the hydrophobic transmembrane and cytoplasmic tail.

For ELISA assays a gp41 fusion protein (LE41) consisting of an amino terminal fragment of the Trp E gene fused to 100 amino acids from the amino terminus of gp41 was expressed in E. coli and purified as previously described. Reduced and carboxymethylated rgp120 and sgp160 were prepared by dialysis of sgp160 and rgp120 into Tris/HC1 buffer containing urea and EDTA. Dithiothreitol (DTT) was added to yield 10 mM final volume, and the proteins were mixed four hours at room temperature. Iodoacetic acid was added to 25 mM final volume, and the samples were dialyzed into ammonium bicarbonate buffer. These proteins were used to coat ELISA plates at 1.0 μg/ml, and the purified monoclonals screened in a standard ELISA protocol.

Both soluble forms of the HIV env protein were affinity purified and then used to immunize commercially available Balb/c mice for the production of monoclonal antibodies (MAbs). Each mouse was immunized with 20 μg of rgp120 or sgp160 (683ΔC.7) intraperitoneally (i.p.) or intravenously (i.v.) and boosted three days prior to fusion. The mouse with the highest antisera titer was selected for fusion. The mouse myeloma line NP3×63–Ag8.653 was fused with spleen cells in a 4:1 ratio using 50% polyethylene glycol, although other commercially available myeloma lines may be utilized according to established procedures. Hybrids were selected for growth with media supplemented with hypoxanthine and azaserine. Positive parental supernatants were identified by screening individual wells against rgp120 or sgp160 in a solid-phase enzyme-linked immunosorbent assay (ELISA). Reactive wells were expanded, cloned by limiting dilution, and the hybridoma cells injected into pristine-primed Balb/c mice. Ascites fluid was collected, pooled, and purified by protein-A column chromatography.

Ten stable monoclonal antibody producing cell lines against 683DC.7 and eleven cell lines were produced over several fusions. They had been initially screened by their ability to bind recombinant gp120/gp160 in solid phase ELISAs. Seventeen of the MAbs reacted with gp120, while the remaining reacted with the gp41 portion of the molecule. Solid phase ELISAs were performed as follows: ELISA microtiter plates were coated with recombinant sgp160, rgp120 or LE41 at 1.0 μg/ml. After blocking with 0.5% BSA/PBS (bovine serum albumin/phosphate-buffered saline), 100 μl of purified antibody was tested at a concentration of 10 μg/ml following a standard ELISA procedure.

Subsequent assays were performed to titrate relative strength of binding of gp120 to CD4, and to determine relative affinities. Purified antibody was titered against rgp120 or sgp160, and the half maximum O.D. was calculated from a titration curve (results not shown).

Additionally, an antigen capture assay was used to select higher affinity antibodies which bind soluble antigen. Dynatech polystyrene removable strip wells were coated with 0.5 μg goat anti-mouse IgG and blocked with 0.5% BSA/PBS. After washing, 100 μl of purified antibody at 10 μg/ml was added and incubated for two hours at 37° C. The strips were washed and labelled with $I^{125}$–683ΔC.7, $10^6$ c.p.m. per well, for two hours at room temperature. Finally, the wells were washed, broken apart and counted on a gamma counter (results not shown).

Nineteen of the MAbs were of the IgG1 isotype while the remaining two were IgG2a. Isotypes were determined by MonoAb-ID EIA kit available from Zymed (South San Francisco, Calif., USA) according to the vendor's protocol for isotype determination. Plates were coated with gp160 at 1.0 μg/ml.

2. Epitope Mapping of Monoclonal Antibodies.

The MAbs described above define approximately eleven epitopes on gp160. In general, various epitope mapping methods were consistent in their results. Based on western data, ELISA assays with reduced and carboxymethylated (RCM) gp160/120, and lambda gt11 mapping, the majority of the antibodies appear to bind linear epitopes. One antibody, 6E10, appears to bind to a conformational epitope although it does retain some reactivity on western blot analysis. Methods and results are as follows.

1. Western Immunoblots: Naturally occurring proteolytic cleavage of gp120 resolves three major polypeptides in a 7.5% polyacrylamide SDS gel. Separated are a 75,000 dalton N-terminal and a 55,000 dalton C-terminal band which comprise gp120. Further cleavage within the 55,000 dalton C-terminal band yields a 35,000 dalton COOH-terminal band. Western blot analysis of the monoclonal antibodies with these proteolytic cleavage fragments of gp120 was useful in the initial mapping of the epitopes.

2. Epitope Cross-Competition ELISA: The MAbs were tested for their ability to compete for epitope binding sites on both the gp120 and 160 proteins. ELISA microtiter plates were coated with sgp160 or rgp120 at 1.0 μg/ml After blocking with BSA/PBS, 50 μl of purified MAb at 100 μg/ml was added and incubated one hour at room temperature. Without washing, 50 μl of each antibody coupled to horseradish-peroxidase was added for an additional hour. The plate was washed, substrate added, and read to 490 nm.

3. Lambda gt11 Mapping. A library was constructed containing randomly expressed portions of the gp160 precursor fused to beta galactosidase. Briefly, the 3.5 kb HTLV-IIIB gp160 region was treated with increasing quantities of DNAse I (described in copending U.S.S.N. 07/448038), blunted with the Klenow fragment of DNA polymerase and 4 deoxynucleotide triphosphates, and ligated to EcoRI oligonucleotide linkers. The material was run on a 5% acrylamide gel, and the 100–1100 bp region of the gel was isolated. DNA in this region was eluted and ligated to 1μg of lambda gt11 EcoR1-cut phage arms. The ligated DNA was packaged in vitro and amplified in E. coli 1088. The library consisted of 1.6×10$^7$ independent phage.

The library was screened by plating approximately 4×10$^3$ phage onto E. coli Y1090 cells. After plaques developed, a nitrocellulose filter impregnated with isopropylthiogalactoside was placed onto the plate and incubated overnight. The filters were blocked and incubated with MAb. Colorimetric detection of the antibody was achieved using horseradish peroxidase conjugated with goat anti-mouse antibody.

Positively reacting phage were plaque purified, and the DNA was isolated. Double-stranded lambda DNA sequencing was carried out at 50° C. with klenow DNA polymerase and dideoxynucelotides in the presence of the following beta galactosidase gene specific oligonucleotide primers: 5'-TTGACACCAGACCAACTGGTAATG-3'(reverse or carboxy-terminus) and 5'-ATGGGGATTGGTGGCGACTCCTGGAGCCCG-3' (forward or amino-terminus). The observed DNA sequence resulted in the coordinates of the inserted gp120 fragment.

4. Peptides: Peptides from various regions of gp120 were either synthesized or isolated by affinity purification of various digests. The peptides were spotted onto nitrocellulose and then reacted with the various monoclonal antibodies. Goat anti-mouse IgG conjugated to horseradish peroxidase or iodinated Protein A was used to probe for reactivity of monoclonal antibodies with the peptides.

5. RCM 160/120: The MAbs were screened by ELISA against reduced carboxymethylated (RCM) gp160/120 to determine if they reacted with linear or conformational epitopes. 683ΔC.7 and rgp120 were dialyzed into Tris/HCl containing urea and EDTA. The following day, dithiothreitol (DTT) was added to yield 10 mM final volume, and the proteins were mixed four hours at room temperature. Iodoacetic acid was added to 25 mM final volume and the samples were mixed 30 minutes in the dark. DTT was added to yield 100 mM final volume, and the samples were dialyzed into ammonium bicarbonate. The proteins were used to coat ELISA plates at 1.0 μg/ml, and the MAbs screened in a standard ELISA protocol.

Results of the epitope mapping are summarized in Table 3.

TABLE 3*

| MAb | Western | Epitope | Lambda gt11 | Peptides | RCM 160/120 |
| --- | --- | --- | --- | --- | --- |
| 1D10 | 120k, 75k | G | a.a. 65–85 | | + |
| 1F9 | 120k, 75k | L | 233–274 | | + |
| 5B3 | 120k, 75k | G(A) | 60–120 | | + |
| 5B6 | 120k, 75k | | | HSV-gD25 | + |
| 5B9 | 120k, 55k | J(A/B/D) | | | + |
| 5C2 | 120, 55, 35k | J(D) | 390–439 | 421–432 | + |
| 5D6 | 120k, 55, | | | | + |
| 5G9 | 120, 55, 35k | | | | N.D. |
| 6D8 | 120k, 75k | K | 86–115 | | + |
| 6E10 | 120k, 75k | B | 60–320 | | − |
| 7F11 | 120, 55, 35k | J(D) | 431–448 | 413–457 | + |
| 7G11 | 129, 55, 35k | J | | | N.D. |
| 9E3 | 160k | H(C) | 542–573 | | + |
| 9F6 | 120k, 75k | L | 240–275 | | + |
| 10C1 | 160k | D(E) | | | + |
| 10D8 | 120k, 75k | A | | 301–324 | + |
| 10F6 | 120k, 75k | A | | 301–324 | + |
| 11G5 | 120k, 75k | A | | 301–324 | + |
| 13H8 | 120k, 75k | F(D/E) | 410–453 | 412–457 | + |
| 14F12 | 160k, 41k | E(D/C) | | | + |
| 15G7 | 160k | C | | | + |

*MAbs in italics were raised against gp120. All others were raised against 683ΔC.7 (gp160).

To further explore the specificity of these antibodies, and to control for the possibility that the preferential reactivity to gp120 or gp160 might represent an artifact peculiar to the ELISA assays, the binding of these antibodies was studied in a liquid phase radioimmunoprecipitation assay (RIP). For these experiments rgp120 and sgp160 were metabolically labeled with [$^{35}$S]-methionine. Both proteins were then mixed together and reacted with the monoclonal antibodies. The resulting antibody antigen complexes were then absorbed to glutaraldehyde fixed S. aureus and the proteins specifically immunoprecipitated were resolved by polyacrylamide gel electrophoresis as previously described. FIG. 5 shows an autoradiograph where the ten monoclonal antibodies to sgp160 were analyzed. It can be seen that three major bands were specifically immunoprecipitated by one or more of the sera tested, a 140 kD band corresponding to sgp160, a 110–120 kD band corresponding to rgp120, and a 75 kD band which represents proteolytic breakdown products of gp120 and sgp160. Previous studies, described above, have indicated that gp120 and sgp160 produced in recombinant cell culture are often clipped between amino acid residues 315–316. In the case of gp120, proteolysis at this residue yields an amino-terminal 75 kD fragment and carboxy-terminal 50 kD fragment which is in turn proteolyzed to smaller fragments. Proteolysis of sgp160 at this residue yields two fragments with a 75 kD mobility (gp75a and gp75b). Comparison of the data in Tables 1 and 2 with that in FIG. 4 revealed that the RIP data correspond very well with the ELISA data and that the monoclonal antibodies 9E3, 10C1, 14F12, and 15G7 all were reactive exclusively with gp160. This result suggests that those antibodies reacted with epitopes on gp41 or with epitopes dependent on the interaction between gp41 and gp120. Thus it is concluded that the selectivity observed could not be attributed to an artifact in the ELISA format.

3. Function of Monoclonal Antibodies.

Six of the monoclonal antibodies inhibited the binding of gp120 to the CD4 receptor. Of these six, three were able to neutralize HIV virions as indicated by a reduction of reverse transcriptase activity in vitro. Three other monoclonal antibodies also neutralized infectious virions in the in vitro reverse transcriptase assays. Assays were performed according to the following procedures.

1. CD4/gp120 binding: Monoclonal antibodies were tested in a solution phase ELISA assay to determine CD4/gp120 blocking ability. ELISA microtiter plates were coated with antibody to CD4 (L104.5) at 1.0 μg/ml. In a separate reaction plate, gp160 or 120 antibodies were incubated with soluble rgp120 overnight at 4° C. Soluble CD4 was added for one hour at room temperature, and the resulting complex was transferred to the L104.5-coated plate. Non-blocked CD4 was detected with a horseradish-peroxidase-conjugated anti-CD4 antibody (Leu3a-HRP). If the CD4/120 binding site was blocked by a gp160/120 antibody, soluble CD4 would bind to the plate and would be detected by the peroxidase conjugate.

2. Syncytia Inhibition Assay: Monoclonal antibodies were tested for their ability to inhibit syncytia formation with HIV(IIIB) infected cells according to known protocols.

3. Reverse Transcriptase Assay: Monoclonal antibodies were tested for in vitro neutralization of HIV in reverse transcriptase (RT) assays. In this assay, various dilutions of antisera were incubated with a stock solution of the IIIB isolate of HIV-1. The antibody-treated virus was then added to a culture of H9 cells as previously described in the literature, and after seven days of culture the reverse transcriptase-specific incorporation of thymidine was measured. Of 10 antibodies tested four were found to inhibit HIV-1 infectivity in this assay. Greatly reduced levels of reverse transcriptase activity in infected CD4+ T-lymphocyte cultures may indicate neutralization of the virus by the monoclonal antibody. A positive result indicates greater than 50% RT inhibition at a minimum 1:10 dilution (approximately 50–100 μg/ml).

Results of these assays are summarized in table 4.

TABLE 4*

| MAb | CD4/gp120 | Syncytia | RT Assay |
|---|---|---|---|
| *1D10* | — | | |
| *1F9* | — | | |
| 5B3 | Inhibits | | Inhibits |
| 5B6 | — | | |
| 5B9 | — | | |
| *5C2* | Inhibits | | |
| 5D6 | — | | |
| 5G9 | — | | |
| 6D8 | — | | |
| 6E10 | Inhibits | | Inhibits |
| *7F11* | Inhibits | | |
| *7G11* | Inhibits | | |
| 9E3 | — | | |
| *9F6* | — | | |
| 10C1 | — | | |
| 10D8 | — | Inhibits | Inhibits |
| 10F6 | — | Inhibits | Inhibits |
| 11G5 | — | Inhibits | Inhibits |
| 13H8 | Inhibits | | Inhibits |
| 14F12 | — | | |
| 15G7 | — | | |

*MAbs in italics were raised against gp120. All others were raised against 683ΔC.7 (gp160).

4. Discussion.

Of the twenty-one monoclonal antibodies defining eleven different epitopes of gp160, nine have identified functional epitopes of gp120 based on the available assays. Six of these antibodies blocked the gp120/CD4 interaction. Of these six, three anti-rgp120 and one anti-683ΔC7 MAb bound a region of gp120 that was defined as critical for CD4 binding (Lasky et al., supra). The two other blocking antibodies 6E10 and 5B3, which were made against 683ΔC.7, appear to bind regions which are not in close sequential proximity to the earlier-reported CD4 binding region. Whether they block sterically or through some other interaction is knot known. The interest in the 6E10 and 5B3 antibodies is further enhanced by their ability to neutralize the virus as indicated in the reverse transcriptase assays. It is possible that these antibodies will define other regions of gp120 critical for infectivity.

The 10D8, 11G5 and 10F6 antibodies, also raised against 683ΔC.7, bind a 24 amino acid region (amino acids 301–324) designated as RP-135 by earlier published reports (Matsushita et al., J Virol. 62(6):2107–2114, 1988). Data from the syncytia inhibition assay was consistent with other reports of antibodies to the RP-135 region. Exactly how this region is involved in neutralization is not understood, however, it is known that it lies outside the gp120/CD4 binding site. More importantly, this region spans the internal gp120 clip cite (at amino acids 315–316). These antibodies, or other antibodies to this region, are used to separate out clipped gp120 when a preparation of unclipped gp120 is desired.

Other monoclonal antibodies bound epitopes on gp120 that are highly conserved among the different isolates, however no function has yet to be assigned to these regions. Although some rgp120 and sgp160 MAbs appear to bind the same epitope, only those raised against sgp160 demonstrate functional activity. This suggests that the 683ΔC.7 molecule may preserve the conformational structure essential for the generation of neutralizing MAbs.

In our studies we explored the cross reactivity of antibodies elicited against the IIIB isolate of HIV-1 with other isolates. Since the sequence of gp120 has been determined for a large number of HIV-1 isolates, cross reactivity data might be useful in epitope mapping studies. For these studies the env genes of five diverse isolates of HIV-1 were mutagenized so as to insert a stop codon near the authentic terminus of gp120. To enhance expression in mammalian cells, the signal sequences were deleted and replaced with that of glycoprotein D of herpes simplex virus type 1 as previously described. The reactivity of these isolates with the monoclonal antibodies to sgp160 was measured in two ways: in a dot blot assay using partially purified envelope glycoprotein coupled to nitrocellulose, and in a radioimmunoprecipitation assay.

To measure the reactivity of the monoclonal antibodies with authentic HIV-1 derived viral proteins, immunoblot strips purchased from Dupont were used. In these studies 10 μl of ascites were diluted to 3 ml in blocking buffer and incubated with the nitrocellulose strips for 1 hour at room temperature. The strips were then washed three times with 3 ml of blocking buffer and then incubated with a 1:1000 dilution of alkaline phosphatase conjugated, affinity-purified, goat anti-mouse immunoglobulin for 1 hour. The strips were then washed three times and stained with a phosphatase developing kit commercially available from Kirlegaar and Perry. Results of this procedure are shown in FIG. 4.

Figure 4:
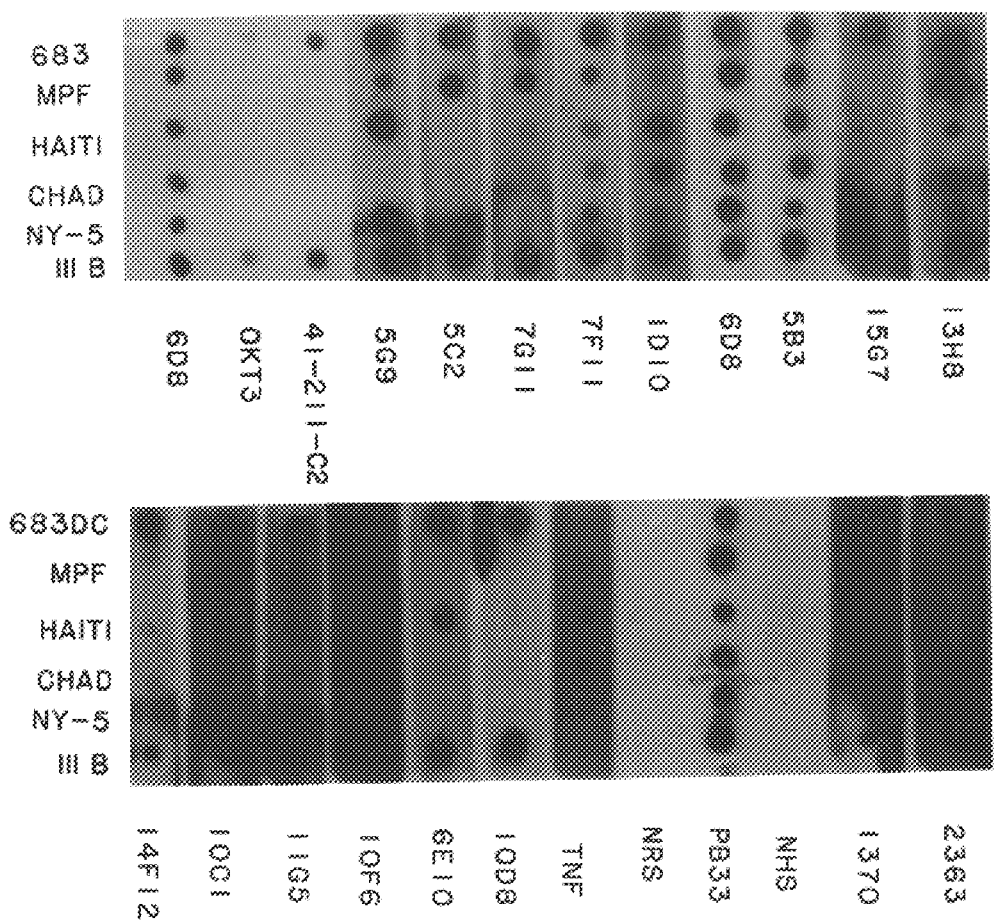
FIG. 4 shows the results of an immunoblot depicting the cross reactivity of the antibodies of this invention with other isolates of HIV-1 besides IIIB.

As can be seen in FIG. 4, monoclonals 13H8 and 5B3 were able to react with all of the isolates tested. Similar analysis was carried out on a number of the monoclonal antibodies to gp120 previously described. In these studies another antibody, 6D8, was found to react with all isolates tested.

To explore the potential that these monoclonal antibodies could be coupled to cytotoxic agents and used as immunotoxin conjugates, the ability of these antibodies to bind to env glycoproteins in the presence of human sera that contains high levels of antibodies to gp120 was measured. To ascertain whether or not monoclonal antibodies to gp120 would be inhibited by the antibodies present in the sera of HIV-1 infected individuals, competitive binding assays were performed. ELISA microtiter plates were coated with gp160 at 1 μg/ml, blocked and washed. Normal human sera was then added at 1:10 or 1:100 and an active fraction of sera from HIV-1 infected individuals was added at 100 μg/ml. Sera was pre-incubated for one hour, and then various concentrations of purified monoclonal antibodies at 100 μg/ml. After a one-hour incubation, plates were washed and antibody detected with GAM-HRP.

We found that the monoclonals were able to bind even in the presence of undiluted human sera. This result was somewhat surprising and suggests that either the monoclonals were directed to epitopes different from those recognized by antibodies in human sera, or that the concentration and/or affinity of a monoclonal antibody to any given epitope is much higher than the concentration and/or affinity of antibodies to any particular epitope in human polyclonal sera. Thus these monoclonals could be passively transferred and are expected to bind to HIV-1 glycoproteins in the presence of high concentrations of human sera.

Example 3. Preparation of Unclipped GP120 Through Recombinant Cell Culture

Recombinant cell culture procedures have been developed which yield unclipped HIV env polypeptides (in this example rgp120) which are substantially free of clipped gp120 fragments. Current approaches to cell culture optimization are found in Mather, *Methods in Enzymology*, vol. 185, chapter 43, pages 567–577 (1990), specifically incorporated by reference.

Chinese hamster ovary cells transfected with an HIV envelope gene expression plasmid (CHO DHFR+) (Lasky, L.A. et al., Science 223: 209; 1986) were used for the production of the rgp120 used in this example. An initial stock spinner culture was initiated at approximately $3.11 \times 10^5$ cells/ml and grown in 1.5 liters of selective medium containing low glucose (3.2 g/l), 7.5% diafiltered fetal bovine serum, and 3.7 ml of 1.0 mM methotrexate. The culture was stored on magnetic stirrer in a 37° C. (30°–41° C.) incubator at approximately 40–50 rpm. After four days, the culture reached a density of approximately $15.0 \times 10^5$ cells/ml (approximately 98% viability). Approximately 800 ml of this stock spinner culture was placed in roller bottles containing about 7200 ml of selective medium as before. Roller bottles were placed on roller racks at speed of approximately 0.3 rpm, at 37° C. (36°–40° C.) for four days. Dulbecco's modified Eagle's medium or Ham's F12/DME GHT⁻ medium is suitable, as are commercially available media designed for the growth of cells frequently used for expression of recombinant proteins such as CHO (e.g., Hana Biologicals CHO medium).

After four days, the selective medium was poured out of the roller bottles, and the bottles were rinsed and then filled with approximately 300 ml of non-selective medium containing high glucose (4.3 g/l), methotrexate as above, and 1% fetal bovine serum. It is currently preferred that this stage of the cell culture be performed in low serum, preferably in media containing approximately 0–3 percent serum, and more preferably 1 percent. The roller bottles were gassed with 100% $CO_2$ at 2–4 psi for approximately 1–3 seconds through sterile pipets, and then placed on roller racks at approximately 0.3 rpm and 37° C. (36°–40° C.).

Cultures were harvested after approximately three days. To harvest, the media in the roller bottles was poured out and filtered through an autoclaved 5.0 micron Millipore and 0.45 micron Sartorious filter, 0.2 g/l sodium azide was added, and the harvest was stored at 2°–8° C. An additional 300 ml of non-selective media was to the roller bottles, and the cultures were incubated as before for an additional three days and then harvested a second time as before.

Harvested materials were concentrated by ultrafiltration, then purified using affinity chromatography as described in Lasky et al., supra 1986. Additional purification procedures were performed, including gel permeation chromatography and anion exchange chromatography, however it was preferred to utilize cation exchange and hydrophobic interaction chromatography (HIC) according to standard protocols as described above.

Purification procedures utilizing the monoclonal antibodies disclosed above, particularly 10F6, 6E10, 10D8 and 11G5, coupled to glycerol-coated controlled pore glass were also performed using published procedures.

We claim:

1. A method for producing unclipped HIV env which is greater than 50% free of clipped HIV env, comprising growing a mammalian cell transformed with DNA encoding unclipped HIV env and competent for replicating and expressing unclipped HIV env, said cell being grown in media with low serum, and recovering unclipped HIV env which is greater than 50% free of clipped HIV env.

2. The method of claim 1, wherein said media contains approximately 0–3 percent serum.

* * * * *